United States Patent
Chi et al.

(10) Patent No.: US 8,822,818 B2
(45) Date of Patent: Sep. 2, 2014

(54) 4,4'-DICARBOXY-2,2'-BIPYRIDINE DERIVED TRIDENTATE LIGAND, METAL COMPLEX CONTAINING THE SAME, AND APPLICATION THEREOF

(75) Inventors: Yun Chi, Hsinchu (TW); Cheng-Xuan Li, Hsinchu (TW); Shen-Han Yang, Hsinchu (TW); Hsin-Pei Wu, Hsinchu (TW); Kuan-Lin Wu, Hsinchu (TW); Chien-Wei Hsu, Hsinchu (TW); Shih-Han Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 363 days.

(21) Appl. No.: 13/306,609

(22) Filed: Nov. 29, 2011

(65) Prior Publication Data

US 2012/0247561 A1    Oct. 4, 2012

(30) Foreign Application Priority Data

Apr. 1, 2011   (TW) .............. 100111578 A

(51) Int. Cl.
| | |
|---|---|
| *C07D 401/14* | (2006.01) |
| *C07D 409/14* | (2006.01) |
| *C07D 495/04* | (2006.01) |
| *C07F 15/00* | (2006.01) |
| *H01L 51/00* | (2006.01) |
| *H01G 9/20* | (2006.01) |

(52) U.S. Cl.
CPC ........... *C07D 401/14* (2013.01); *H01L 51/0037* (2013.01); *C07D 495/04* (2013.01); *C07D 409/14* (2013.01); *Y02E 10/542* (2013.01); *H01G 9/2059* (2013.01); *Y02E 10/549* (2013.01); *C07F 15/0053* (2013.01); *H01L 51/0086* (2013.01); *H01G 9/2031* (2013.01)
USPC .............. 136/263; 546/10; 546/167; 546/256

(58) Field of Classification Search
None
See application file for complete search history.

(56) References Cited

U.S. PATENT DOCUMENTS

| | | | |
|---|---|---|---|
| 7,812,251 B2 * | 10/2010 | Islam et al. .................... | 136/263 |
| 2005/0081911 A1 | 4/2005 | Islam et al. | |
| 2009/0107552 A1 | 4/2009 | Minns et al. | |
| 2010/0010643 A1 | 1/2010 | Pomerantz et al. | |

* cited by examiner

*Primary Examiner* — Kamal Saeed
(74) *Attorney, Agent, or Firm* — Birch Stewart Kolasch & Birch, LLP

(57) ABSTRACT

Disclosed is a 4,4'-dicarboxy-2,2'-bipyridine derived tridentate ligand represented by formula (I):

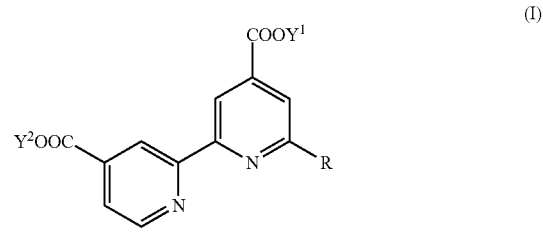

wherein definitions of $Y^1$, $Y^2$, and R are the same as those defined in the specification.
Also disclosed are a metal complex containing the aforesaid tridentate ligand and a dye-sensitized solar cell containing the metal complex.

13 Claims, 4 Drawing Sheets

4,4'-DICARBOXY-2,2'-BIPYRIDINE DERIVED TRIDENTATE LIGAND, METAL COMPLEX CONTAINING THE SAME, AND APPLICATION THEREOF

CROSS-REFERENCE TO RELATED APPLICATION

This application claims priority of Taiwanese Application No. 100111578, filed on Apr. 1, 2011.

BACKGROUND OF THE INVENTION

1. Field of the Invention

This invention relates to a tridentate ligand, more particularly to a 4,4'-dicarboxy-2,2'-bipyridine derived tridentate ligand. The invention also relates to a metal complex containing the tridentate ligand, and a dye-sensitized solar cell containing the metal complex.

2. Description of the Related Art

Photovoltaic cells, sometimes called solar cells, are being increasingly developed in the art due to the fact that sunlight to be converted into electrical energy via the photovoltaic cells is inexhaustible. A dye-sensitized solar cell (DSSC) is one of the photovoltaic cells having most potential. The dye contained in the DSSC is used to absorb visible and near infrared light from the sun to excite electrons. The excited electrons are then injected into a conduction band of a semiconductor electrode so as to produce photocurrent. Therefore, the photovoltaic conversion efficiency of the DSSC is affected primarily by the performance of the dye.

Ruthenium complex containing a tridentate ligand is commonly used as a dye for the dye-sensitized solar cell because superior synthetic productivity and better photovoltaic conversion efficiency can be obtained thereby as compared to a complex containing a bidentate or tetradentate ligand.

US 2009/0107552A1 discloses metal complexes used as a dye for the dye-sensitized solar cell. One set of the metal complexes has a formula of $MX_3L$, wherein M is a transition metal ion, each X is independently a monodentate ligand selected from the group consisting of thiocyanate, isothiocyanate, and optionally substitutable pyridine, and L is a tridentate ligand having a formula defined therein. A compound having a following formula is specifically illustrated:

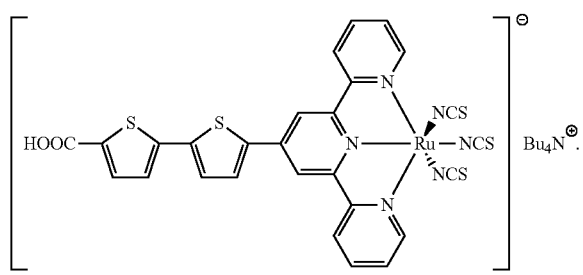

The extinction coefficient of the compound is about 13,600 at $\lambda_{max}$ of 612 nm. The photovoltaic conversion efficiency of a solar cell containing the compound is about 3.9%.

As shown in the above formula, there is only one carboxyl group (COOH) or carboxylate ion ($CO_2^-$) in the terpyridine ligand of the ruthenium complex. Therefore, the terpyridine ligand can not be effectively bonded to the anode made of titanium dioxide nanoparticles. Furthermore, a conjugate group (i.e., a dithiophene group) intervening between the carboxyl group (or the carboxylate ion) and the terpyridine ligand is required, thereby resulting in a long distance between ruthenium and the carboxyl group (or the carboxylate ion) which is to be bonded to titanium dioxide. It might be due to such a relatively long distance which the generated photoelectrons have to travel, that a reduction in the voltage and the current intensity produced by the solar cell is possible. Furthermore, it is desirable to enhance the photovoltaic conversion efficiency and the absorption at both the visible and near infrared regions of the aforesaid ruthenium complex. Such a stringent demand for panchromatic absorption has thus been achieved by addition of thiocyanate ligand. Moreover, the thiocyanate ligands contained in the ruthenium complex have a relatively weak coordination bonding strength, and thus can not firmly chelate with the ruthenium atom. Therefore, the efficiency and the lifespan of the dye-sensitized solar cell produced thereby need further improvement.

On the other hand, an anionic complex $\{Bu_4N\}_3[Ru(Htctpy)(NCS)_3]$, $H_3tctpy=4,4',4"$-tricarboxy-2,2':6,2"-terpyridine, known as a black dye or a N749 dye, has also been used in the art of the dye-sensitized solar cell. Three carboxy groups are contained in the anionic complex.

It is found by the inventors of the present invention that terpyridine ligand substituted with only two carboxy groups can vest the complex with desirably superior properties, e.g., bonding to the $TiO_2$ electrode. In accordance with the present invention, it is uncovered that by reducing the number of carboxy as the substituent group on terpyridine from three to two, while incorporating a highly conjugated n-electron donating appendage at the third carboxy-free pyridine moiety, the solar energy harvesting capability can be significantly and desirably improved, without encountering the drawbacks in the prior art as mentioned above.

SUMMARY OF THE INVENTION

Therefore, an object of the present invention is to provide a 4,4'-dicarboxy-2,2'-bipyridine derived tridentate ligand having improved conjugation and enhanced extinction coefficient.

Another object of the present invention is to provide a metal complex containing the 4,4'-dicarboxy-2,2'-bipyridine derived tridentate ligand and having improved absorption at visible and near infrared regions and enhanced extinction coefficient.

A further object of the present invention is to provide a dye-sensitized solar cell containing the metal complex of this invention.

According to the first aspect of this invention, there is provided a 4,4'-dicarboxy-2,2'-bipyridine derived tridentate ligand represented by formula (I):

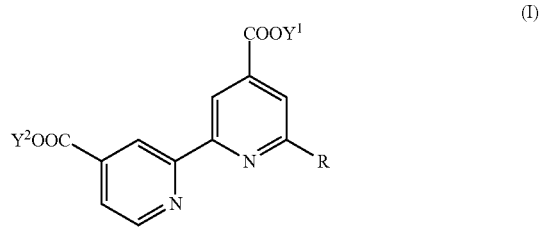

wherein $Y^1$ and $Y^2$ independently represent hydrogen or a $C_1$-$C_8$ straight or branched chain alkyl group; and R represents

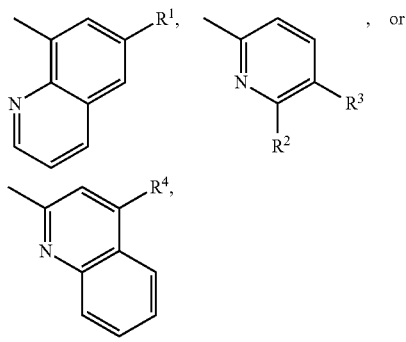

wherein
R¹ and R⁴ independently represent hydrogen, a halogen atom, trifluoromethyl, a carboxylic group, or a $C_1$-$C_{12}$ straight or branched chain alkyl group; and
one of R² and R³ is hydrogen, and the other of R² and R³ is a $C_1$-$C_{12}$ straight or branched chain alkyl group, an alkoxy group, an alkylsulfenyl group,

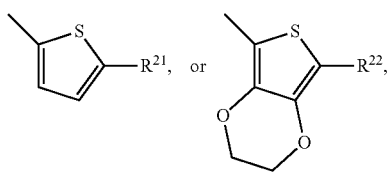

wherein
$R^{21}$ and $R^{22}$ independently represent a $C_1$-$C_{12}$ straight or branched chain alkyl group, an alkoxy group, an alkylsulfenyl group, or

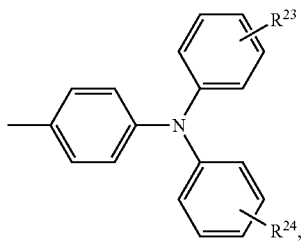

wherein
$R^{23}$ and $R^{24}$ independently represent hydrogen, or a $C_1$-$C_{12}$ straight or branched chain alkyl group, an alkoxy group, or an alkylsulfenyl group.

According to the second aspect of this invention, there is provided a metal complex containing the aforesaid tridentate ligand and represented by formula (II) or formula (III):

$$ML^1(L^2)_3 \quad (II), or$$

$$ML^1L^3 \quad (III)$$

wherein
M represents ruthenium or osmium;
$L^1$ represents a 4,4'-dicarboxy-2,2'-bipyridine derived tridentate ligand defined above;
$L^2$ represents a monodentate ligand; and $L^3$ represents

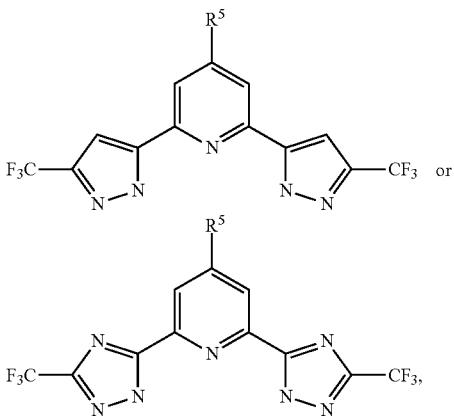

wherein
$R^5$ represents hydrogen, a $C_1$-$C_{12}$ straight or branched chain alkyl group, an aryl group, an alkoxy group, an alkylsulfenyl group, a dialkylamino group, a functionalized alkanoyl group,

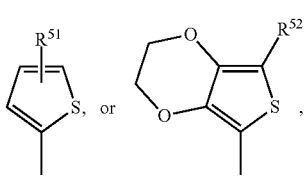

wherein
$R^{51}$ and $R^{52}$ independently represent a $C_1$-$C_{12}$ straight or branched chain alkyl group, an alkoxy group, or an alkylsulfenyl group.

According to the third aspect of this invention, there is provided a dye-sensitized solar cell including an electrolyte, a first electrode, and a second electrode. The first electrode is disposed in the electrolyte, and includes a transparent conductive substrate, a porous film disposed on the transparent conductive substrate, and the aforesaid metal complex adsorbed on the porous film. The second electrode is disposed in the electrolyte and is spaced apart from the first electrode.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
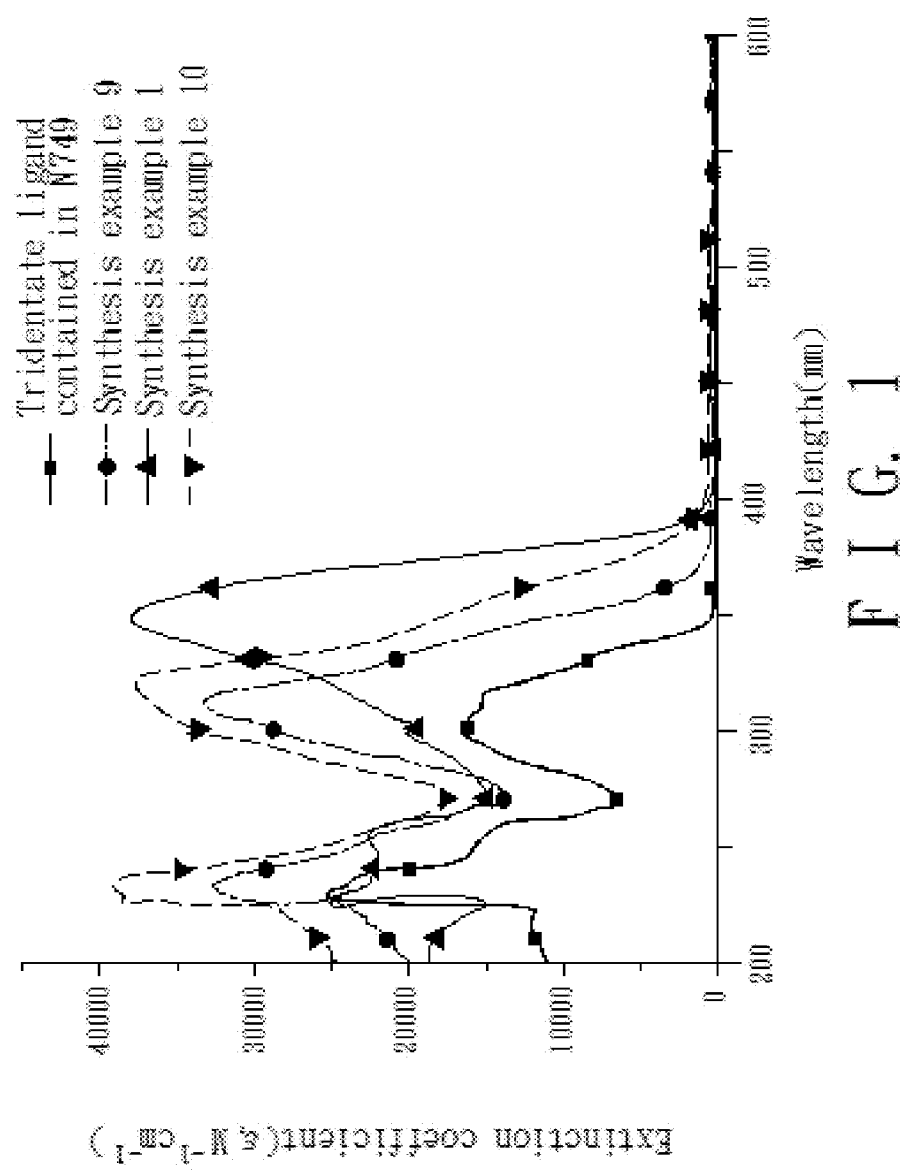
FIGS. 1 and 2 are graphs illustrating the absorption spectra of the examples of tridentate ligands according to the present invention and a conventional tridentate ligand.

The 4,4'-dicarboxy-2,2'-bipyridine derived tridentate ligand of the present invention is represented by formula (I):

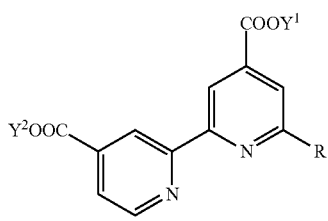

(I)

wherein
Y$^1$ and Y$^2$ independently represent hydrogen or a C$_1$-C$_8$ straight or branched chain alkyl group; and
R represents

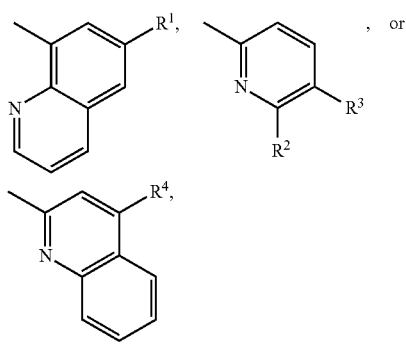

wherein
R$^1$ and R$^4$ independently represent hydrogen, a halogen atom, trifluoromethyl, a carboxylic group, or a C$_1$-C$_{12}$ straight or branched chain alkyl group; and
one of R$^2$ and R$^3$ is hydrogen, and the other of R$^2$ and R$^3$ is C$_1$-C$_{12}$ straight or branched chain alkyl group, an alkoxyl group,

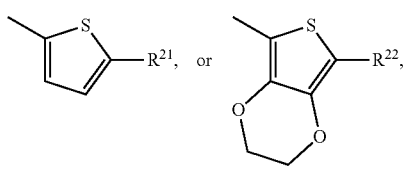

wherein
R$^{21}$ and R$^{22}$ independently represent a C$_1$-C$_{12}$ straight or branched chain alkyl group, an alkoxy group, an alkylsulfenyl group, or

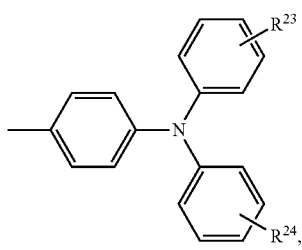

wherein
R$^{23}$ and R$^{24}$ independently represent hydrogen, a C$_1$-C$_{12}$ straight or branched chain alkyl group, an alkoxy group, or an alkylsulfenyl group.

Preferably, R is

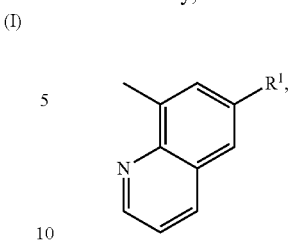

wherein R$^1$ is hydrogen, a halogen atom, trifluoromethyl, a carboxylic group, or a C$_1$-C$_{12}$ straight or branched chain alkyl group.

Preferably, R is

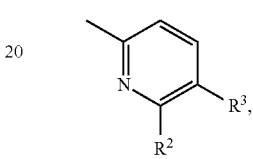

wherein R$^2$ is

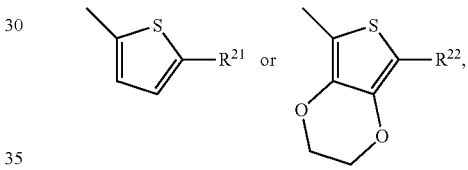

and R$^3$ is hydrogen.

Preferably, R$^2$ is

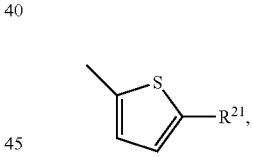

wherein R$^{21}$ is a C$_1$-C$_{12}$ straight or branched chain alkyl group, an alkoxy group, an alkylsulfenyl group, or

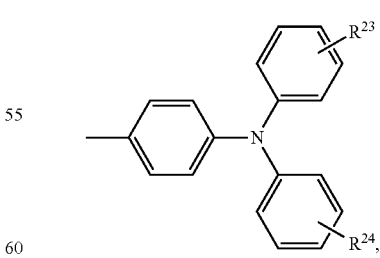

wherein R$^{23}$ and R$^{24}$ independently represent hydrogen, a C$_1$-C$_{12}$ straight or branched chain alkyl group, an alkoxy group, or an alkylsulfenyl group. More preferably, R$^{21}$ is a C$_1$-C$_{12}$ straight or branched chain alkyl group.

Preferably, $R^2$ is

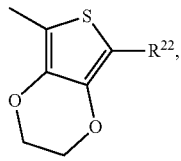

wherein $R^{22}$ is a $C_1$-$C_{12}$ straight or branched chain alkyl group, an alkoxy group, an alkylsulfenyl group, or

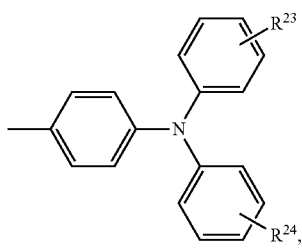

wherein $R^{23}$ and $R^{24}$ independently represent hydrogen, a $C_1$-$C_{12}$ straight or branched chain alkyl group, an alkoxy group, or an alkylsulfenyl group. More preferably, $R^{22}$ is a $C_1$-$C_{12}$ straight or branched chain alkyl group.

Preferably, R is

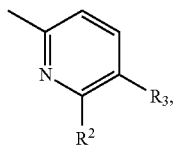

wherein $R^2$ is hydrogen, and $R^3$ is $C_1$-$C_{12}$ straight or branched chain alkyl group, an alkoxyl group,

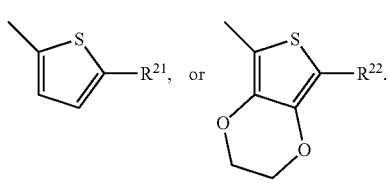

Preferably, $R^3$ is

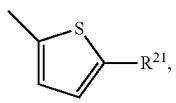

wherein $R^{21}$ is a $C_1$-$C_{12}$ straight or branched chain alkyl group, an alkoxy group, an alkylsulfenyl group, or

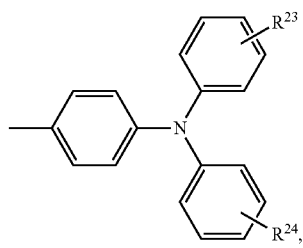

wherein $R^{23}$ and $R^{24}$ independently represent hydrogen, a $C_1$-$C_{12}$ straight or branched chain alkyl group, an alkoxy group, or an alkylsulfenyl group. More preferably, $R^{21}$ is a $C_1$-$C_{12}$ straight or branched chain alkyl group or

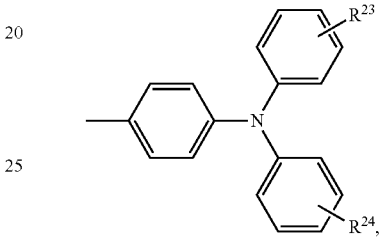

wherein $R^{23}$ and $R^{24}$ independently represent hydrogen or an alkoxy group.

Preferably, $R^3$ is

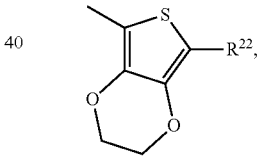

wherein $R^{22}$ is a $C_1$-$C_{12}$ straight or branched chain alkyl group, an alkoxy group, an alkylsulfenyl group, or

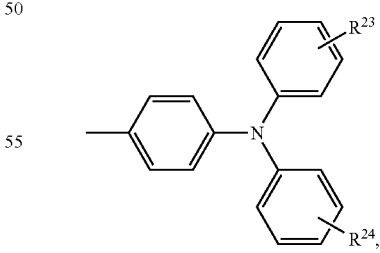

wherein $R^{23}$ and $R^{24}$ independently represent hydrogen, a $C_1$-$C_{12}$ straight or branched chain alkyl group, an alkoxy group, or an alkylsulfenyl group. More preferably, $R^{22}$ is a $C_1$-$C_8$ straight or branched chain alkyl group or

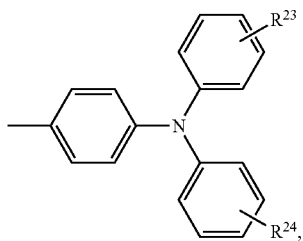
wherein $R^{23}$ and $R^{24}$ independently represent an alkoxy group.
Preferably, R is
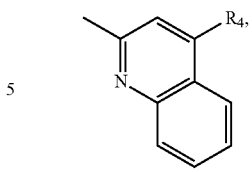
wherein $R^4$ is hydrogen, a halogen atom, trifluoromethyl, a carboxylic group, or a $C_1$-$C_{12}$ straight or branched chain alkyl group.
Illustrated examples of the tridentate ligand of the present invention include, but are not limited to,
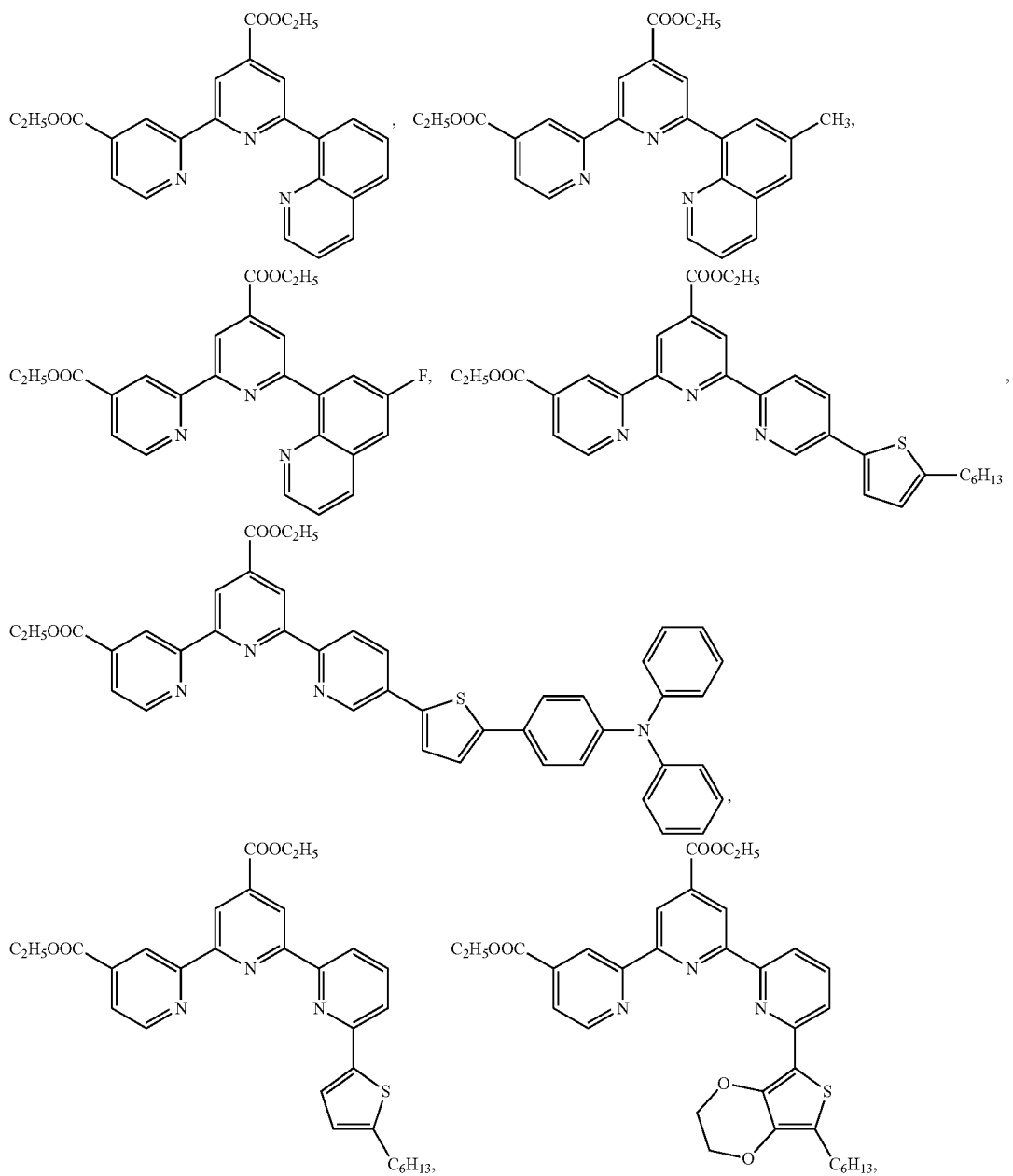

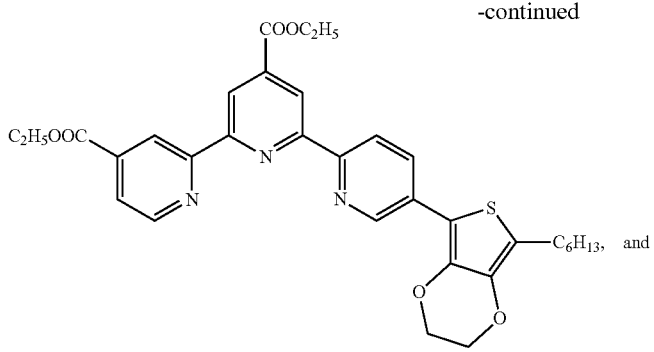

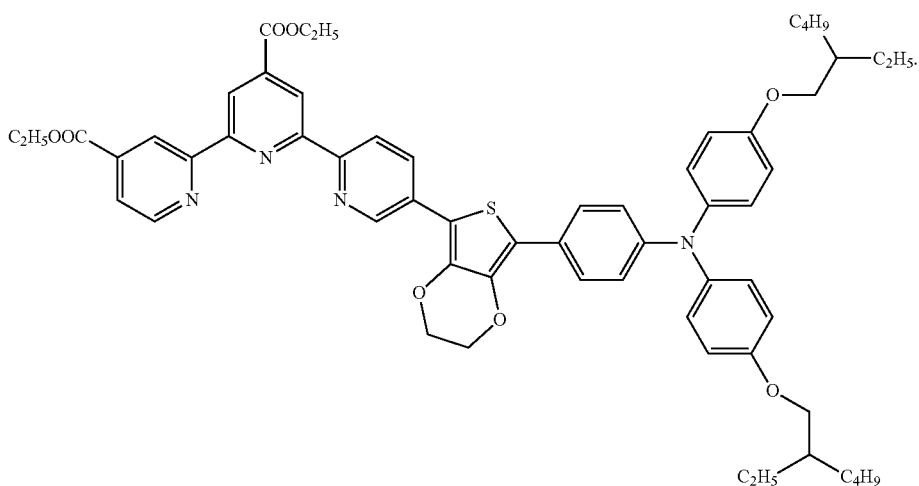

The tridentate ligand of the present invention can be prepared using suitable reactants and under suitable reaction conditions. Such suitable reactants and reaction conditions can be selected according to the specific substituents on the tridentate ligand to be introduced. The preparation of the tridentate ligand of the present invention can be conducted in a manner well known in the art, preferably by the following steps: (1) subjecting a first reactant and an organometallic agent to a reaction under a basified condition to form an intermediate, and (2) mixing a second reactant and the intermediate to form a mixture and subjecting the mixture to a reaction under heating in the presence of a catalyst for the C—C bond coupling.

The first reactant is selected from

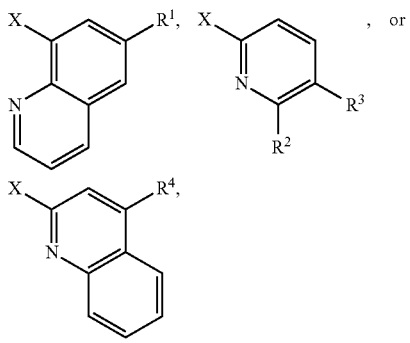, or

wherein X represents a halogen atom. The second reactant is selected from 4,4'-carboxy-2,2'-bipyridine halide, or 4,4'-carboxylate-2,2'-bipyridine halide.

Preferably, the organometallic agent is selected from tributyltin chloride, hexa-n-butylditin, or the like. Preferably, a reagent suitable for providing the basified condition for C—C bond coupling is n-butyl lithium (referred to as n-BuLi hereinafter). A reaction catalyst can be optionally added in step (1). Preferably, the reaction catalyst is tetrakis(triphenylphosphine) palladium, or the like.

Preferably, the catalyst used in step (2) is selected from $Pd(PPh_3)_4$, cuprous iodide, bis(triphenylphosphine) palladium (II)dichloride, e.g. $PdCl_2(PPh_3)_2$, bis(tri-tert-butylphosphine) palladium, or combinations thereof.

The metal complex of the present invention is represented by formula (II) or formula (III):

$$ML^1(L^2)_3 \qquad (II), or$$

$$ML^1L^3 \qquad (III)$$

wherein

M represents ruthenium or osmium;

$L^1$ represents a 4,4'-dicarboxy-2,2'-bipyridine derived tridentate ligand defined above;

$L^2$ represents a monodentate ligand; and $L^3$ represents

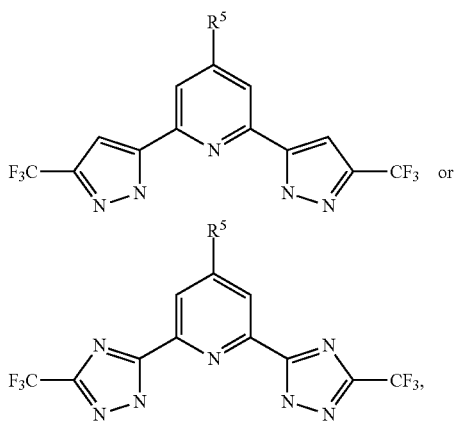

wherein
R[5] represents hydrogen, a $C_1$-$C_{12}$ straight or branched chain alkyl group, an aryl group, an alkoxy group, an alkylsulfenyl group, a dialkylamino group, a functionalized alkanoyl group,

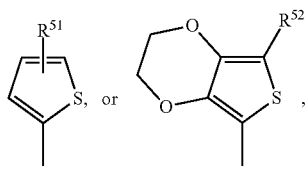

wherein
$R^{51}$ and $R^{52}$ independently represent a $C_1$-$C_{12}$ straight or branched chain alkyl group, an alkoxy group, or an alkylsulfenyl group.

Preferably, $L^2$ is thiocyanate.

Preferably, $R^{51}$ and $R^{52}$ independently represent a $C_1$-$C_{12}$ straight chain alkyl group, an alkoxy group, or an alkylsulfenyl group.

Generally, a metal complex containing divalent ruthenium as the central metal atom is used as a dye for a dye-sensitized solar cell. Its absorption spectrum covers most of the visible spectrum. The oxidation and reduction energy levels of these ruthenium complexes are suitable for the introduction of electrons into the porous titanium dioxide electrode and for the reduction of the oxidized dye by the redox couple present in the electrolyte solution. Osmium has chemical properties similar to those of ruthenium due to both of them belong to the elements of Group 8 metal family. Therefore, a dye-sensitized solar cell having similar performance can be obtained via the replacement of osmium for ruthenium.

Preferably, the metal complex also contains a complexing counter ion. There is no specific limitation to the complexing counter ion as long as the charge equivalence of the metal complex can be obtained. Preferably, the complexing counter ion is selected from a tetrabutylammonium ion, a sodium ion, or a potassium ion.

The metal complex can be prepared via the selection of suitable reactants and reaction conditions according to the specific tridentate ligand, and the method for the preparation of the metal complex can be conducted using a technique well known in the art. Generally, the method for the preparation of the metal complexes includes the steps of mixing the tridentate ligand with a metal source reagent to obtain a mixture and subjecting the mixture to a reaction condition under heating in the presence of a catalyst. Preferably, the metal resource is selected from a ruthenium or osmium source. Preferably, the ruthenium source is selected from ruthenium trichloride hydrate (referred to as Ru(III)Cl$_3$.H$_2$O hereinafter), tetrakis (dimethyl sulfoxide)dichloro ruthenium (referred to as Ru(II) Cl$_2$(DMSO)$_4$ hereinafter), or the like. Preferably, the osmium source is selected from osmium trichloride (referred to as Os(III)Cl$_3$ hereinafter), or the like. After the preparation of the metal complex, the ester functional group on the tridentate ligand can be hydrolyzed into a carboxyl anion (CO$_2^-$) or carboxylic acid (COOH) group using a base agent. Preferably, the base agent is selected from a sodium hydroxide (NaOH) solution, a terabutylammoniumhydroxide (TABOH) solution, or the like.

The tridentate ligand of the present invention can be used to effectively modulate the energy level of the highest occupied molecular orbital (referred to as HOMO hereinafter) of the metal complex so as to raise or reduce the energy level of HOMO and to reduce the band gap between the energy level of HOMO and the energy level of the lowest unoccupied molecular orbital (referred to as LUMO hereinafter) of the metal complex. Furthermore, the metal-to-ligand charge transfer process can be used to raise the charge separation efficiency so that the metal complex can have better light absorption at visible and infrared regions and have relatively high extinction coefficient. Furthermore, there are two CO$_2$H and/or CO$_2^-$ groups on the tridentate ligand of the present invention. Therefore, the tridentate ligand of the present invention can be relatively strongly bonded onto the titanium oxide electrode of the dye-sensitized solar cell as compared to the aforesaid example of the metal complex disclosed in US 2009/0107552A1 in which there is only one such CO$_2$H group on the tridentate ligand of the example of the metal complex of the prior art. Furthermore, the CO$_2$H and/or CO$_2^-$ groups are directly bonded onto the pyridine portion in the tridentate ligand of the present invention. Therefore, the distance between the CO$_2$H and/or CO$_2^-$ groups and the central metal can be reduced thereby. The problem of the loss of photoelectrons encountered in the aforesaid prior art can be reduced, and the voltage and the current intensity produced by the solar cell can be increased by using the metal complex of the present invention.

Moreover, as described above, the thiocyanate ligands contained in the ruthenium complex disclosed in US 2009/0107552A1 possess a relatively weak coordination bond strength, and thus can not firmly interact to the ruthenium. Therefore, the efficiency and the lifespan of the dye-sensitized solar cell produced thereby are inferior. On the contrary, when the aforesaid metal complex of formula (III) of the present invention is used, the efficiency and the lifespan of the dye-sensitized solar cell produced thereby can be improved since no thiocyanate ligand is contained in the metal complex.

The dye-sensitized solar cell of the present invention includes an electrolyte, a first electrode, and a second electrode.

Preferably, the electrolyte is composed of 1,2-dimethyl-3-propylimidazolium iodide (DMPII, 0.6M), lithium iodide (LiI, 0.1M), I$_2$ (0.05M), and tert-butylpyridine (0.5M) dissolved in a mixture of acetonitrile and valeronitrile in a volume ratio of 85:15.

The first electrode is disposed in the electrolyte, and includes a transparent conductive substrate, a porous film disposed on the transparent conductive substrate, and the aforesaid metal complex deposited on the porous film. The second electrode is disposed in the electrolyte and is spaced apart from the first electrode. Preferably, the material for the porous film is selected from titanium dioxide (referred to as TiO$_2$ herein after), indium tin oxide, or the like. Preferably, the material for the transparent conductive substrate is selected from a flexible polymeric material or a rigid material. Examples of the flexible polymeric material include, but are not limited to, polyethylene, polypropylene, polyimide, polymethyl methacrylate, polycarbonate, polyethylene terephthalate, or the like. Examples of the rigid material include, but are not limited to, glass, or the like.

The following examples are provided to illustrate the preferred embodiments of the invention, and should not be construed as limiting the scope of the invention.

EXAMPLES

Preparation Example 1

4-ethylpyridine (125 mL) was added into a 150 mL one-necked flask, and was distilled at a temperature of 55° C. under a pressure of 0.2 torr to obtain purified 4-ethylpyridine. Purified 4-ethylpyridine (90 mL) and Pd/C (10 g) were metered into another 150 ml one-necked flask, and were refluxed at a temperature of 190° C. under an argon atmosphere for 9 days. The temperature in the flask was reduced to room temperature and Pd/C was filtered out to obtain a filtrate, which was purified via Kugelrohr filtration at a temperature of 180° C. under a pressure of 0.2 torr to obtain a colorless liquid (33 g), which was confirmed to be 4,4'-diethyl-2,2'-bipyridine (yield: 39.34%).

Spectral analysis data of 4,4'-diethyl-2,2'-bipyridine: $^1$H NMR (400 MHz, CDCl$_3$, 298 K), δ (ppm): 8.54 (d, $J_{HH}$=8.0 Hz, 2H), 8.22 (d, $J_{HH}$=8.0 Hz, 2H), 7.12 (s, 2H), 2.70 (q, $J_{HH}$=8.0 Hz, 4H), 1.28 (t, $J_{HH}$=8.0 Hz, 6H).

4,4'-diethyl-2,2'-bipyridine (3 g, 14.1 mmol) was added into a 500 mL conical flask. Concentrated sulfuric acid (40 mL) and K$_2$Cr$_2$O$_7$ (16.64 g, 56.4 mmol) were sequentially added into the conical flask in an ice bath. After complete addition, the temperature was raised back to room temperature, and was then raised to a temperature of 70° C. Stirring was conducted at a temperature of 70° C. for 3 hours. The temperature was then reduced to room temperature. The mixture in the conical flask was poured into crushed ice, and was allowed to stand for 12 hours. Precipitate was collected via suction filtration, and was then rinsed with deionized water followed by drying to obtain a white powder (3.2 g), which was confirmed to be 4,4'-dicarboxylic acid-2,2'-bipyridine (yield: 95%).

4,4'-dicarboxylic acid-2,2'-bipyridine was added into a 250 mL one-necked flask, and absolute ethanol (100 mL) was then added. Concentrated sulfuric acid (4 mL) was then slowly added. Reflux was conducted at a temperature of 100° C. for 2 days. The temperature was then reduced to room temperature. Solvent was removed in vacuo and neutralization was conducted by slowly adding saturated aqueous sodium carbonate solution. Precipitate was collected via filtration and was rinsed with deionized water to obtain a white solid (3.65 g), which was confirmed to be 4,4'-bis(ethoxycarbonyl)-2,2'-bipyridine (yield: 86%).

Spectral analysis data of 4,4'-bis(ethoxycarbonyl)-2,2'-bipyridine: $^1$H NMR (400 MHz, CDCl$_3$, 298K), δ (ppm): 8.93 (d, $J_{HH}$=8.0 Hz, 2H), 8.84 (d, $J_{HH}$=8.0 Hz, 2H), 7.89 (d, $J_{HH}$=4.0 Hz, 2H), 4.44 (q, $J_{HH}$=8.0 Hz, 4H), 1.44 (t, $J_{HH}$=8.0 Hz, 6H).

The obtained white solid was added into a 250 ml two-necked flask, and was dissolved by adding anhydrous methylene chloride. A solution of mCPBA (3.4 g, 19.7 mmol) dissolved in methylene chloride was slowly dripped into the flask in an ice bath using an isobaric liquid feeder. The temperature was raised to room temperature and stirring was conducted for 24 hours. Solvent was removed and methylene chloride was further added. An organic layer was obtained after washing with saturated saline solution. The solvent was removed under reduced pressure and the crude product was purified by column chromatography on silica gel (using ethyl acetate:CH$_2$Cl$_2$=1:2 as eluent) to obtain a white solid (2 g, yield: 52%).

Spectral analysis data of the white solid: $^1$H NMR (400 MHz, CDCl$_3$, 298K), δ (ppm): 9.27 (s, 1H), 8.88 (d, $J_{HH}$=4.0 Hz, 1H), 8.73 (d, $J_{HH}$=4.0 Hz, 1H), 8.32 (d, $J_{HH}$=8.0 Hz, 1H), 7.93 (d, $J_{HH}$=4.0 Hz, 1H), 7.87 (d, $J_{HH}$=4.0 Hz, 1H), 4.41 (q, $J_{HH}$=8.0 Hz, 4H), 1.40 (t, $J_{HH}$=8.0 Hz, 6H).

The chemical structure of the white solid was confirmed to be

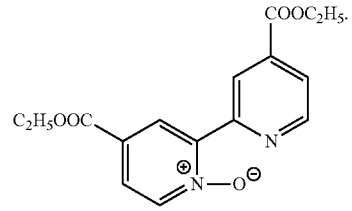

The obtained white solid (1.53 g, 4.8 mmol) was added into a 150 mL one-necked flask, and POCl$_3$ (50 mL) was then added. Heating was conducted under reflux for 12 hours. The temperature was then reduced to room temperature. The solvent was removed under reduced pressure, and saturated aqueous sodium carbonate solution was slowly added under an ice bath until neutralization was reached. Methylene chloride was then added. An organic layer was obtained after washing with saturated saline solution. The solvent was removed under reduced pressure and the crude product was purified by column chromatography (using methylene chloride as eluent) to obtain 6-chloro-4,4'-bis(ethoxycarbonyl)-2,2'-bipyridine as a white solid (1.51 g, yield: 93%).

Spectral analysis data of 6-chloro-4,4'-bis(ethoxycarbonyl)-2,2'-bipyridine: $^1$H NMR (400 MHz, CDCl$_3$, 298K), δ (ppm): 8.90 (d, $J_{HH}$=8.0 Hz, 1H), 8.88 (s, 1H), 8.84 (d, $J_{HH}$=8.0 Hz, 1H), 7.91~7.92 (m, 2H), 4.53 (q, $J_{HH}$=8.0 Hz, 4H), 1.43 (t, $J_{HH}$=8.0 Hz, 6H).

6-chloro-4,4'-bis(ethoxycarbonyl)-2,2'-bipyridine (2 g, 5.97 mmol) was added into a 150 mL one-necked flask, and propionitrile (50 mL) and bromotrimethyl silane (6.6 ml, 47.7 mmol) were then added. Heat was conducted under reflux for 2 days. The temperature was then reduced to room temperature. The solution in the flask was poured into an iced sodium hydroxide solution (2.0M). Precipitate in the solution was collected via filtration, and was then washed with deionized water and dried to obtain a white solid (2.1 g, yield: 93%).

Spectral analysis data of the white solid: $^1$H NMR (400 MHz, CDCl$_3$, 298K), δ (ppm): 8.89~8.87 (m, 2H), 8.83 (d, $J_{HH}$=4.8 Hz, 1H), 8.06 (d, $J_{HH}$=1.6 Hz, 1H), 7.90 (d, $J_{HH}$=1.6 Hz, 1H), 4.44 (q, $J_{HH}$=8.0 Hz, 4H), 1.42 (t, $J_{HH}$=8.0 Hz, 6H).
The chemical structure of the white solid was confirmed to be

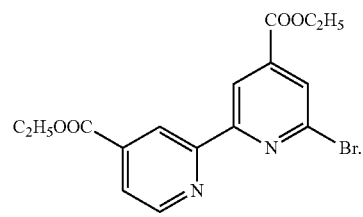

Preparation Example 2

2-hexylthiophene (4.29 g, 25.5 mmol) was added into a 150 ml two-necked flask, which was then purged with nitrogen three times. Anhydrous tetrahydrofuran (referred to as THF hereinafter) was then added. The temperature was reduced to −78° C. n-BuLi (12.21 mL, 30.5 mmol) was slowly added. Stirring was conducted for 30 minutes. 2-isopropoxy-4,4,5,5-tetramethyl-1,3,2-dioxaborolane (6.05 mL, 30.5 mmol) was then added. The temperature was slowly raised to room temperature, and stirring was conducted for 6 hours. THF was removed under reduced pressure, and methylene chloride was added. An organic layer was obtained after washing with a saline solution. The solvent was removed under reduced pressure to obtain a pink oil (5.57 g, yield: 75.8%).

Spectral analysis data of the pink oil: $^1$H NMR (400 MHz, CDCl$_3$, 298K), δ (ppm): 7.45 (d, J$_{HH}$=3.2 Hz, 1H), 6.84 (d, J$_{HH}$=3.2 Hz, 1H), 2.85 (t, J$_{HH}$=8.0 Hz, 2H), 1.70~1.63 (m, J$_{HH}$=8.0 Hz, 2H), 1.23~1.31 (m, 16H), 0.91~0.85 (m, 5H). The chemical structure of the pink oil was confirmed to be

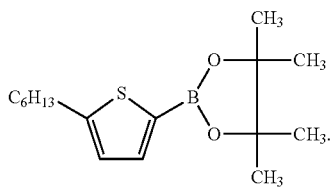

The obtained pink oil (2.3 g, 7.81 mmol), 2-bromo-5-iodopyridine (2.01 g, 7.10 mmol), and Pd(PPh$_3$)$_4$ (0.41 g, 0.36 mmol) were added into a 150 mL two-necked flask, which was then purged with nitrogen three time. Anhydrous THF and an aqueous K$_2$CO$_3$ solution (28.4 mL, 56.8 mmol) were then added. Heating was conducted under reflux for 12 hours. After reaction was completed, solvent was removed under reduced pressure, and methylene chloride was added. An organic layer was obtained after washing with saline solution. The solvent was removed under reduced pressure and the crude product was purified by column chromatography (using ethyl acetate:hexane=1:3 as eluent) to obtain a yellow solid (1.82 g, yield: 79.3%).

Spectral analysis data of the yellow solid: $^1$H NMR (400 MHz, CDCl$_3$, 298K), δ (ppm): 8.53 (d, J$_{HH}$=2.8 Hz, 1H), 7.64 (d, J$_{HH}$=2.4 Hz, 1H), 7.43 (d, J$_{HH}$=8.4 Hz, 1H), 7.14 (d, J$_{HH}$=3.2 Hz, 1H), 6.76 (d, J$_{HH}$=3.6 Hz, 1H), 2.80 (t, J$_{HH}$=7.6 Hz, 1H), 1.69~1.63 (m, 2H), 1.27~1.38 (m, 6H), 0.89~0.87 (m, 3H). The chemical structure of the yellow solid was confirmed to be

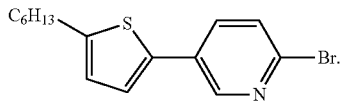

Preparation Example 3

3,4-ethylenedioxythiophene (3.5 g, 24.6 mmol) was added into a 250 mL two-necked flask, which was then purged with nitrogen three times. Anhydrous THF was added. The temperature was reduced to −78° C. n-BuLi (10.4 mL, 23.42 mmol) was slowly added, and stirring was conducted for 30 minutes. 1-bromohexane (3.81 mL, 23.42 mmol) was slowly added. The temperature was slowly raised to room temperature, and stirring was conducted for 6 hours. Solvent was removed under reduced pressure, and methylene chloride was next added. An organic layer was obtained after washing with saline solution. The solvent was removed under reduced pressure and the crude product was purified by column chromatography (using ethyl acetate:hexane=1:20 as eluent) to obtain a light yellow oil (2.1 g, yield: 39%).

Spectral analysis data of the light yellow oil: $^1$H NMR (400 MHz, CDCl3, 298K), δ (ppm): 6.09 (s, 1H), 4.15 (t, J$_{HH}$=8.0 Hz, 4H), 2.60 (t, J$_{HH}$=8.0 Hz, 2H), 1.61~0.90 (m, 11H). The chemical structure of the light yellow oil was confirmed to be

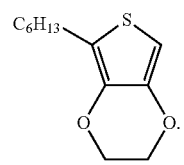

The obtained light yellow oil (4.26 g, 18.8 mmol) was added into a 150 mL two-necked flask, which was then purged with nitrogen three times. Anhydrous THF was added, and the temperature was then reduced to −78° C. n-BuLi (6.06 mL, 20.7 mmol) was slowly added, and stirring was conducted for 30 minutes. Tributyltin chloride (5.91 mL, 20.7 mmol) was added. The temperature was slowly raised to room temperature, and stirring was conducted for 6 hours. Solvent was removed under reduced pressure, and chloroform was added. An organic layer was obtained after washing with saline solution. The solvent was removed under reduced pressure and the crude product was dried with anhydrous magnesium sulfate to obtain yellowish oil (9.5 g). The chemical structure of the yellowish oil was confirmed to be

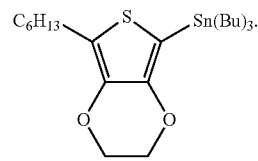

The obtained yellow oil (7.14 g, 13.8 mmol), 2-bromo-2-iodopyridine (3.0 g, 10.6 mmol), and Pd (PPh$_3$)$_2$Cl$_2$ (0.75 g, 1.06 mmol) were added into a 250 ml two-necked flask, which was then purged with nitrogen three times. Anhydrous DMF was added, and the temperature was then raised to 80° C. Reflux was conducted for 12 hours. Solvent was removed under vacuum, and CH$_2$Cl$_2$ was added. An organic layer was obtained after washing with saline solution. The solvent was removed under reduced pressure and the crude product was purified by column chromatography (using ethyl acetate:hexane=1:5 as eluent) to obtain a yellow solid (2.14 g, yield: 53%).

Spectral analysis data of the yellow solid: $^1$H NMR (400 MHz, CDCl$_3$, 298K), δ (ppm): 8.63 (d, J$_{HH}$=4.0 Hz, 1H), 7.80 (d, J$_{HH}$=8.0 Hz, 1H), 7.36 (d, J$_{HH}$=8.0 Hz, 1H), 4.30 (t, J$_{HH}$=8.0 Hz, 2H), 4.23 (t, J$_{HH}$=8.0 Hz, 2H), 2.63 (t, J$_{HH}$=7.6 Hz, 2H), 1.63~0.87 (m, 11H). The chemical structure of the yellow solid was confirmed to be

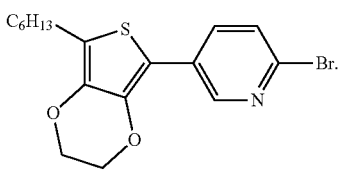

Preparation Example 4

Sodium 3-nitrobenzenesulfonate (3.9 g, 17.34 mmol) was added into a reaction vessel. Methanesulfonic acid (30 mL) was added with stirring to substantially dissolve the contents in the reaction vessel. $FeSO_4 \cdot 7H_2O$ (0.23 g, 0.83 mmol) was then added. 2-bromoaniline (3 mL, 27.52 mmol) was slowly dripped into the reaction vessel. Stirring was conducted for 30 minutes. A further methanesulfonic acid was added until the contents in the reaction vessel were completely dissolved. The temperature was raised to 118-125° C. Gylcerol (5.02 mL, 68.8 mmol) was slowly dripped. The temperature was then raised to 125-133° C. and stirring was conducted for 10-16 hours. The temperature was then reduced to room temperature. Dilution was conducted with cold dd $H_2O$. 10 M of sodium hydroxide and solka folc (cellulose) were added into the reaction vessel in an ice bath. 1M of a sodium hydrogen carbonate solution was next added until neutralization was reached. Crude product was washed with a substantial amount of ethyl acetate. Filtrate was collected via suction filtration, and was washed with a substantial amount of ethyl acetate and water. An organic layer was collected. The solvent was removed under reduced pressure and the crude product was purified by column chromatography (using ethyl acetate:hexane=1:1 as eluent) to obtain a brown oil (4.7 g, 22.7 mmol, yield: 83%).

Spectral analysis data of the brown oil: $^1$H NMR (400 MHz, $CDCl_3$, 298K), δ (ppm): 9.09 (dd, $J_{HH}$=4.0, 1.5 Hz, 1H), 8.20 (dd, $J_{HH}$=8.4, 1.6 Hz, 1H), 8.06 (dd, $J_{HH}$=7.6, 1.2 Hz, 1H), 7.80 (dd, $J_{HH}$=8.4, 1.2 Hz, 1H), 7.50 (dd, $J_{HH}$=8.4, 4.0 Hz, 1H), 7.42 (t, $J_{HH}$=8.0 Hz, 1H). The chemical structure of the brown oil was confirmed to be

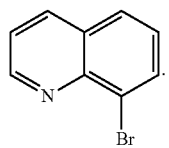

Preparation Example 5

Sodium 3-nitrobenzenesulfonate (3.4 g, 15.24 mmol) was added into a reaction vessel. Methanesulfonic acid (40 mL) was added with stirring to substantially dissolve the contents in the reaction vessel. $FeSO_4 \cdot 7H_2O$ (0.20 g, 0.73 mmol) was then added. 2-bromo-4-methylaniline (3 mL, 24.19 mmol) was slowly added. Stirring was conducted for 30 minutes. A further methanesulfonic acid was added until the contents in the reaction vessel were completely dissolved. The temperature was raised to 118-125° C. Gylcerol (5.02 mL, 68.8 mmol) was slowly added. The temperature was then raised to 125-133° C. and stirring was conducted for 10-16 hours. The temperature was then reduced to room temperature. Dilution was conducted with ice cold deionized water. 10 M of a sodium hydroxide solution and solka folc were added into the reaction vessel in an ice bath. 1M of a sodium hydrogen carbonate solution was next added until neutralization was reached. Crude product was washed with a substantial amount of ethyl acetate. Filtrate was collected via suction filtration, and was washed with a substantial amount of ethyl acetate and water. An organic layer was collected. The solvent was removed under reduced pressure and the crude product was purified by column chromatography (using ethyl acetate:hexane=3:1 as eluent) to obtain a yellow oil (4.9 g, 22.3 mmol, yield: 93%). The chemical structure of the yellow oil was confirmed to be

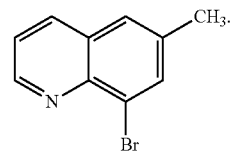 [SMILES: Cc1cc(Br)c2ncccc2c1]

Preparation Example 6

Sodium 3-nitrobenzenesulfonate (6.2 g, 27.7 mmol) was added into a reaction vessel. Methanesulfonic acid (50 ml) was added with stirring to substantially dissolve the contents in the reaction vessel. $FeSO_4 \cdot 7H_2O$ (0.37 g, 1.32 mmol) was then added. 2-bromo-4-fluoroaniline (5 mL, 43.9 mmol) was slowly dripped into the reaction vessel. Stirring was conducted for 30 minutes. A further methanesulfonic acid was added until the contents in the reaction vessel were completely dissolved. The temperature was raised to 118-125° C. Gylcerol (8.02 mL, 109.9 mmol) was slowly dripped. The temperature was then raised to 125-133° C. and stirring was conducted for 10-16 hours. The temperature was then reduced to room temperature. Dilution was conducted with ice cold deionized water. 10 M of a sodium hydroxide solution and solka folc were added into the reaction vessel in an ice bath. 1 M of a sodium hydrogen carbonate solution was added until neutralization was reached. Crude product was washed with a substantial amount of ethyl acetate. Filtrate was collected via suction filtration, and was washed with a substantial amount of ethyl acetate and water. An organic layer was collected. The solvent was removed under reduced pressure and the crude product was purified by column chromatography (using ethyl acetate:hexane=1:1 as eluent) to obtain a white solid (8.8 g, 39.07 mmol, yield: 89%).

Spectral analysis data of the white solid: $^1$H NMR (400 MHz, $CDCl_3$, 298K), δ (ppm): 8.99 (dd, $J_{HH}$=4.0, 2.4 Hz, 1H), 8.11 (dd, $J_{HH}$=8.0, 1.6 Hz, 1H), 7.87 (dd, $J_{HH}$=8.4, 2.8 Hz, 1H), 7.47 (dd, $J_{HH}$=8.4, 4 Hz, 1H), 7.43 (dd, $J_{HH}$=8.4, 5.6 Hz, 1H); $^{19}$F NMR (376 MHz, $CDCl_3$, 298K), δ (ppm): 112.14 (s, 1F). The chemical structure of the white solid was confirmed to be

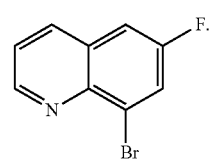 [SMILES: Fc1cc(Br)c2ncccc2c1]

Preparation Example 7

2,6-dibromopyridine (5.92 g, 24.9 mmol) was added into a two-necked flask. Vacuuming and then filling of nitrogen were repeated three times. Anhydrous THF (25 ml) was added. A solution of i-PrMgCl (12.5 mL, 24.9 mmol, 2.0M, dissolved in dimethyl ether) was dripped at room temperature. Reaction was conducted for 2 hours. Tributyltin chloride (7.11 mL, 24.9 mmol, purity: 95%) was then dripped at room temperature. Reaction was conducted for 18 hours. Reaction was then ceased by adding water. THF was removed via rotary evaporation. Hexane was then added, and washing was conducted three times with deionized water. An organic layer was collected and was dehydrated using anhydrous magnesium sulfate. Filtrate was obtained via filtration, and was concentrated to obtain a brown oily liquid, which was purified via micro-distillation at 155° C. and at 0.2 torr to obtain a yellow oily liquid.

2-bromo-5-hexylthiophene (0.554 g, 2.24 mmol) was added into a 50 mL two-necked flask. Vacuuming and then filling of nitrogen were repeated three times. Anhydrous THF (15 mL) was added. The temperature was reduced to −78° C. A solution of n-BuLi (2.06 mL, 5.15 mmol, 2.5 M, dissolved in hexane) was dripped. The color of the solution turned to be dark brown. The temperature was raised by removal from the ice bath, and reaction was conducted for 20 minutes. The temperature was reduced to −78° C. again. A solution of $ZnCl_2$ (0.397 g, 2.91 mmol) in anhydrous THF was dripped. The solution turned yellow. The ice bath was removed, and the reaction was conducted for 90 minutes. The yellow oily liquid (1 g, 2.24 mmol) and Pd $(PPh_3)_4$ (0.127 g, 0.11 mmol) were added. The reaction was conducted for 1 hour, and was then ceased by adding deionized water (about 1 ml). THF was removed via rotary evaporation, and hexane was added. The solution was washed with water. The organic layer was collected and dehydrated using anhydrous magnesium sulfate. Filtrate was obtained via filtration, and was concentrated to remove solvent. The crude product was purified by $Al_2O_3$ column chromatography (using hexane as eluent) to obtain an orange oil (0.853 g, yield: 71%, purity: 77%).

Spectral analysis data of the orange oil: $^1$H NMR (900 MHz, CDCl3, 298K), δ (ppm): 7.42~7.39 (m, 2H), 7.36 (d, J=3.6 Hz, 1H), 7.18 (dd, J=4.8 Hz, 1.6 Hz, 1H), 6.75 (d, J=3.6 Hz, 1H), 2.81 (t, J=8 Hz, 2H), 1.72~0.85 (m, 38H). The chemical structure of the orange oil was confirmed to be

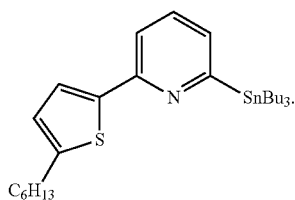

Preparation Example 8

2,6-dibromopyridine (5.92 g, 24.9 mmol) was added into a two-necked flask. Vacuuming and then filling of nitrogen were repeated three times. Anhydrous THF (25 mL) was added. A solution of i-PrMgCl (24.9 mmol, 12.5 ml, 2.0 M, dissolved in dimethyl ether) was dripped at room temperature. Reaction was conducted for 2 hours. Tributyltin chloride (7.06 mL, 24.9 mmol, purity: 95%) was then dripped at room temperature. Reaction was conducted for 18 hours. Reaction was ceased by adding water. THF was removed via rotary evaporation. Hexane was then added, and washing was conducted three times with deionized water. An organic layer was collected and dehydrated using anhydrous magnesium sulfate. Filtrate was obtained via filtration, and was concentrated to obtain a brown oily liquid, which was purified via micro-distillation at 155° C. and at 0.2 torr to obtain a yellow oily liquid (6.5 g).

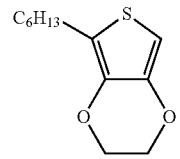

(0.3 g, 1.3 mmol) was added into a 50 ml two-necked flask. Vacuuming and then filling of nitrogen were repeated three times. Anhydrous THF (15 mL) was added. The temperature was reduced to −78° C. A solution of n-BuLi (0.57 mL, 1.44 mmol, 2.5M, dissolved in hexane) was dripped. The color of the solution turned light yellow. The temperature was raised by removal from the ice bath, and reaction was conducted for 20 minutes. The temperature was reduced to −78° C. again. A solution of $ZnCl_2$ (0.232 g, 1.71 mmol) in anhydrous THF was dripped. The ice bath was removed, and the reaction was conducted for 90 minutes. The yellow oily liquid (1 g, 2.24 mmol), $PdCl_2$ (0.006 g, 0.036 mmol), and 1,1'-di(phenylphosphino)ferrocene (0.020 g, 0.036 mmol) were added. The color of the solution turned from light yellow to black. The reaction was conducted for 1 hour, and was then ceased by adding deionized water (about 1 mL). THF was removed via rotary evaporation, and methylene chloride was added. The solution was washed with water. The organic layer was collected and dehydrated using anhydrous magnesium sulfate. Filtrate was obtained via filtration, and was concentrated to remove solvent. Orange oil was obtained (0.539 g, yield: 50%).

Spectral analysis data of the orange oil: $^1$H NMR (400 MHz, CDCl$_3$, 298K), δ (ppm): 7.65 (d, J=8 Hz, 1H), 7.38 (t, J=8 Hz, 1H), 7.08 (d, J=8 Hz, 1H), 4.30~4.28 (m, 2H), 4.28~4.21 (m, 2H), 2.65~2.58 (m, 4H), 1.63~1.28 (m, 38H). The chemical structure of the orange oil was confirmed to be

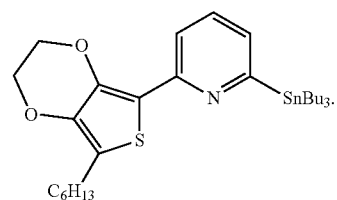

Preparation of Tridentate Ligand

Synthesis Example 1

The product obtained in Preparation Example 2 (0.5 g, 1.54 mmol) was added into a 150 ml two-necked flask, which was then purged with nitrogen three times. Anhydrous THF was added. The temperature was then reduced to −78° C. n-BuLi (0.72 mL, 1.86 mmol) was slowly added. Stirring was conducted for 30 minutes. Tributyltin chloride (0.53 mL, 1.86 mmol) was then slowly added. The temperature was then slowly raised to room temperature, and stirring was conducted for 6 hours. THF was removed under reduced pressure. Dissolution was conducted using methylene chloride.

The organic layer was washed with saline solution. Methylene chloride was removed under reduced pressure to obtain a yellow oil (0.86 g).

The obtained yellow oil (0.990 g, 1.85 mmol), the product obtained in Preparation Example 1 (0.539 g, 1.42 mmol), and Pd(PPh$_3$)$_4$ (0.22 g, 0.19 mmol) were added into a 150 ml two-necked flask, which was then purged with nitrogen three times. Anhydrous toluene was added. Heating was conducted under reflux for 24 hours. Solvent was removed under reduced pressure. Dissolution was conducted with methylene chloride. Extraction was conducted using saline solution to obtain an organic layer. The solvent was removed under reduced pressure to obtain a crude product, which was purified by column chromatography (using ethyl acetate:hexane=1:4 as eluent) followed by recrystallization using hexane to obtain a white solid (0.4 g, yield: 40%).

Spectral analysis data of the white solid: $^1$H NMR (400 MHz, CDCl$_3$, 298K), δ (ppm): 9.11 (s, 1H), 9.05 (s, 1H), 8.98 (d, $J_{HH}$=6.4 Hz, 2H), 8.97 (d, $J_{HH}$=2.4 Hz, 1H), 8.88 (d, $J_{HH}$=4.8 Hz, 1H), 8.65 (d, $J_{HH}$=7.6 Hz, 1H), 8.04 (d, $J_{HH}$=7.6 Hz, 1H), 7.90 (d, $J_{HH}$=4.8 Hz, 1H), 7.30 (d, $J_{HH}$=3.6 Hz, 1H), 6.82 (d, $J_{HH}$=3.6 Hz, 1H), 4.45~4.51 (m, 4H), 2.85 (t, $J_{HH}$=3.6 Hz, 2H), 1.75~1.67 (m, 2H), 1.29~1.48 (m, 12H), 0.89 (t, $J_{HH}$=7.6 Hz, 3H). The chemical structure of the white solid was confirmed to be

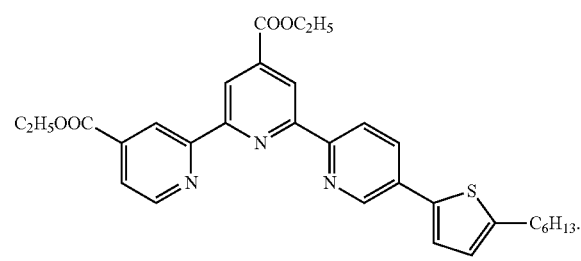

Synthesis Example 2

The product obtained in Preparation Example 3 (0.36 g, 0.94 mmol) was added into a 150 mL two-necked flask, which was then purged with nitrogen three times. Anhydrous THF was added. The temperature was then reduced to −78° C. n-BuLi (0.41 mL, 1.03 mmol) was slowly added. Stirring was conducted for 30 minutes. Tributyltin chloride (0.3 mL, 1.03 mmol) was then added. The temperature was then slowly raised to room temperature, and stirring was conducted for 6 hours. THF was removed under reduced pressure. Dissolution was conducted using methylene chloride. Extraction was conducted using saline solution to obtain an organic layer, which was dehydrated using anhydrous magnesium sulfate. Solvent was removed under reduced pressure to obtain a yellow oil (0.71 g).

The obtained yellow oil (0.71 g, 1.20 mmol), the product obtained in Preparation Example 1 (0.35 g, 0.96 mmol), and Pd(PPh$_3$)$_4$ (0.11 g, 0.01 mmol) were added into a 150 ml two-necked flask, which was then purged with nitrogen three times. Anhydrous dimethylformamide (referred to as DMF hereinafter) was added. The temperature was raised to 80° C., and reaction was conducted for 12 hours. Solvent was removed under vacuum. Dissolution was conducted with methylene chloride. Extraction was conducted using saline solution to obtain an organic layer. The solvent was removed under reduced pressure to obtain a crude product, which was purified by column chromatography (using ethyl acetate:hexane=1:1 as eluent) to obtain a white solid (0.11 g, yield: 20%).

Spectral analysis data of the white solid: $^1$H NMR (400 MHz, CDCl$_3$, 298K), δ (ppm): 9.10 (s, 1H), 9.05 (d, $J_{HH}$=4.0 Hz, 1H), 9.0 (d, $J_{HH}$=4.0 Hz, 1H), 8.94 (d, $J_{HH}$=4.0 Hz, 1H) 8.86 (d, $J_{HH}$=8.0 Hz, 1H), 8.60 (d, $J_{HH}$=8.0 Hz, 1H), 8.11 (d, $J_{HH}$=8.0 Hz, 1H), 7.90 (d, $J_{HH}$=8.0 Hz, 1H), 4.48 (m, 4H), 4.35~4.25 (m, 4H), 2.69 (t, $J_{HH}$=8.0 Hz, 2H), 0.87~1.65 (m, 17H). The chemical structure of the white solid was confirmed to be

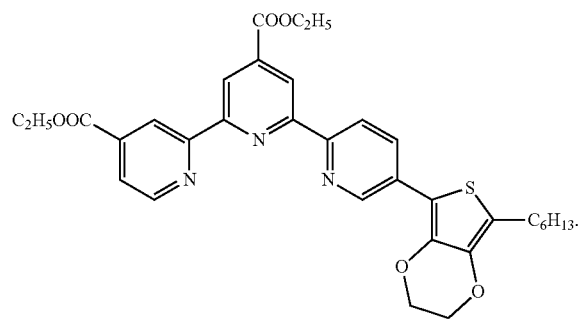

Synthesis Example 3

The product obtained in Preparation Example 4 (1 g, 4.83 mmol) and Pd (PPh$_3$)$_4$ (0.3 g, 0.24 mmol) were added into a reaction vessel and was dissolved by adding anhydrous toluene (40 mL). Hexa-n-butylditin (2.08 mL, 5.31 mmol) was then added. The temperature was raised to 110° C. under nitrogen and reflux was conducted for 24 hours. The temperature was then reduced to room temperature. Suction filtration was then conducted to obtain solid and filtrate, which were then respectively washed with substantial amounts of ethyl acetate and saturated sodium carbonate solution. An organic layer of each of the filtrates was collected. Solvent was removed from the organic layer under reduced pressure. Column chromatography was conducted using hexane as eluent to obtain a colorless oil (1.7 g, 4.07 mmol, yield: 84%).

The obtained colorless oil (0.61 g, 1.46 mmol), the product obtained in Preparation Example 1 (0.5 g, 1.33 mmol), Pd(PPh$_3$)$_4$ (0.15 g, 0.13 mmol), and cuprous iodide (0.05 g, 0.26 mmol) were added into a reaction vessel. Anhydrous DMF (30 mL) was then added. The temperature was raised to 80° C., and reaction was conducted for 15 hours. DMF was removed under reduced pressure. Washing was conducted using ethyl acetate and saturated sodium carbonate solution. Suction filtration was then conducted to obtain solid and filtrate, which were then respectively washed with substantial amounts of ethyl acetate and saturated sodium carbonate solution. An organic layer of each of the filtrates was collected. Solvent was removed from the organic layer under reduced pressure. Column chromatography was conducted using ethyl acetate:hexane=1:2 as eluent to obtain a white solid (0.303 g, 0.71 mmol, yield: 53%).

Spectral analysis data of the white solid: $^1$H NMR (400 MHz, CDCl$_3$, 298K), δ (ppm): 9.06 (s, 1H), 8.98 (d, $J_{HH}$=4.0 Hz, 1H), 8.95 (s, 1H), 8.86 (d, $J_{HH}$=4.0 Hz, 1H), 8.78 (s, 1H), 8.33 (d, $J_{HH}$=4.0 Hz, 1H), 8.24 (d, $J_{HH}$=8.0 Hz, 1H), 7.93 (d, $J_{HH}$=8.0 Hz, 1H), 7.87 (d, $J_{HH}$=4.0 Hz, 1H), 7.72 (t, $J_{HH}$=8.0 Hz, 1H), 7.45 (dd, $J_{HH}$=8.0, 4.0 Hz, 1H), 4.43 (m, 4H), 1.41 (m, 6H). The chemical structure of the white solid was confirmed to be

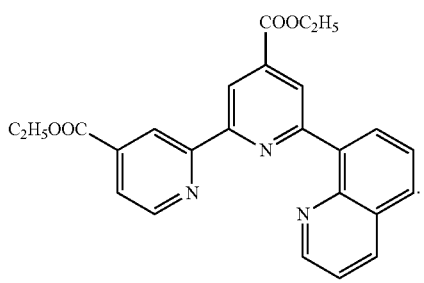

Synthesis Example 4

The product obtained in Preparation Example 5 (2 g, 9.09 mmol) and Pd(PPh$_3$)$_4$ (0.53 g, 0.45 mmol) were added into a reaction vessel and was dissolved by adding anhydrous toluene (50 mL). Hexa-n-butylditin (5.05 mL, 10.00 mmol) was then added. The temperature was raised to 110° C. under nitrogen and reflux was conducted for 24 hours. The temperature was then reduced to room temperature. Suction filtration was then conducted to obtain solid and filtrate, which are then respectively washed with substantial amounts of ethyl acetate and saturated sodium carbonate solution. An organic layer of each of the filtrates was collected. Solvent was removed from the organic layer under reduced pressure. Column chromatography was conducted using hexane as eluent to obtain a yellow oil (3.5 g, 8.18 mmol, yield: 90%).

The obtained clear yellow oil (0.252 g, 0.58 mmol), the product obtained in Preparation Example 1 (0.2 g, 0.53 mmol), Pd(PPh$_3$)$_4$ (0.061 g, 0.05 mmol), and cuprous iodide (0.020 g, 0.11 mmol) were added into a reaction vessel. Anhydrous DMF (20 ml) was then added. The temperature was raised to 80° C., and reaction was conducted for 15 hours. DMF was removed under reduced pressure. Washing was conducted using ethyl acetate and saturated sodium carbonate solution. Suction filtration was then conducted to obtain solid and filtrate, which were then respectively washed with substantial amounts of ethyl acetate and saturated sodium carbonate solution. An organic layer of each of the filtrates was collected. Solvent was removed from the organic layer under reduced pressure. Column chromatography was conducted using ethyl acetate:hexane=1:2 as eluent to obtain a white solid (0.070 g, 0.16 mmol, yield: 30%).

Spectral analysis data of the white solid: $^1$H NMR (400 MHz, CDCl$_3$, 298K), δ (ppm): 9.05 (s, 1H), 8.99 (b, 1H), 8.94 (d, J$_{HH}$=1.2 Hz, 1H), 8.82 (d, J$_{HH}$=5.2 Hz, 1H), 8.72 (d, J$_{HH}$=1.2 Hz, 1H), 8.22 (d, J$_{HH}$=6.8 Hz, 1H), 8.15 (d, J$_{HH}$=2.0 Hz, 1H), 7.89 (dd, J$_{HH}$=5.2, 1.6 Hz, 1H), 7.73 (s, 1H), 7.48 (b, 1H), 4.44 (m, 4H), 1.42 (m, 6H). The chemical structure of the white solid was confirmed to be Synthesis Example 5

The product obtained in Preparation Example 6 (2 g, 8.85 mmol) and Pd(PPh$_3$)$_4$ (0.51 g, 0.44 mmol) were added into a reaction vessel and were dissolved by adding anhydrous toluene (50 mL). Hexa-n-butyl-ditin (3.8 mL, 9.73 mmol) was then added. The temperature was raised to 110° C. under nitrogen and reflux was conducted for 24 hours. The temperature was then reduced to room temperature. Suction filtration was then conducted to obtain solid and filtrate, which were then respectively washed with substantial amounts of ethyl acetate and saturated sodium carbonate solution. An organic layer of each of the filtrates was collected. Solvent was removed from the organic layer under reduced pressure. Column chromatography was conducted using hexane as eluent to obtain a colorless oil (3.47 g, 7.96 mmol, yield: 90%).

The obtained colorless oil (0.254 g, 0.58 mmol), the product obtained in Preparation Example 1 (0.2 g, 0.53 mmol), Pd(PPh$_3$)$_4$ (0.061 g, 0.05 mmol), and cuprous iodide (0.02 g, 0.11 mmol) were added into a reaction vessel. Anhydrous DMF (20 mL) was then added. The temperature was raised to 80° C., and reaction was conducted for 13 hours. DMF was removed under reduced pressure. Washing was conducted using ethyl acetate and saturated sodium carbonate solution. Suction filtration was then conducted to obtain solid and filtrate, which were then respectively washed with substantial amounts of ethyl acetate and saturated sodium carbonate solution. An organic layer of each of the filtrates was collected. Solvent was removed from the organic layer under reduced pressure. Column chromatography was conducted using ethyl acetate:hexane=1:2 as eluent to obtain a white solid (0.111 g, 0.25 mmol, yield: 47%).

Spectral analysis data of the white solid: $^1$H NMR (400 MHz, CDCl$_3$, 298K), δ (ppm): 9.04 (t, J$_{HH}$=8.0 Hz, 1H), 8.97 (d, J$_{HH}$=1.6 Hz, 1H), 8.94 (dd, J$_{HH}$=4, 1.6 Hz, 1H), 8.73 (dd, J$_{HH}$=4.8, 0.8 Hz, 1H), 8.40 (d, J$_{HH}$=1.2 Hz, 1H), 8.17 (m, 2H), 7.89 (dd, J$_{HH}$=4.8, 1.6 Hz, 1H), 7.53 (dd, J$_{HH}$=8.4, 1.4 Hz, 1H), 7.45 (dd, J$_{HH}$=8.4, 4.0 Hz, 1H), 4.45 (m, 4H), 1.41 (m, 6H); $^{19}$F NMR (376 MHz, CDCl$_3$, 298K), δ (ppm): ~112.93 (s, 1F). The chemical structure of the white solid was confirmed to be

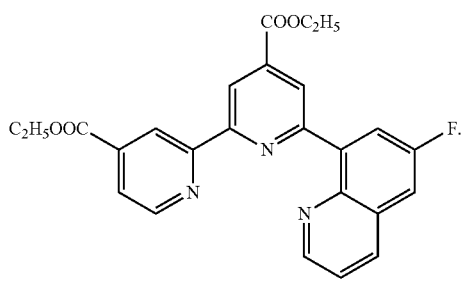

Synthesis Example 6

2-bromoquinoline (1.04 g, 5 mmol) was dissolved by adding anhydrous THF (30 mL). n-BuLi (2.2 mL, 5.5 mmol, 2.5 M in hexane) was slowly added under nitrogen at −78° C. The temperature was maintained at −78° C. for 1 hour. Tributyltin chloride (1.76 mL, 6.5 mmol) was then slowly added, and stirring was conducted at room temperature overnight. Solvent was removed via concentration under reduced pressure. Washing was conducted three times using water and ethyl acetate (40 mL). An organic layer was collected. Solvent was removed from the organic layer under reduced pressure to obtain a colorless oil (1.70 g, yield: 81%).

The colorless oil (0.265 g, 0.58 mmol) thus obtained, the product obtained in Preparation Example 1 (0.2 g, 0.53 mmol), Pd(PPh$_3$)$_4$ (0.061 g, 0.05 mmol), and cuprous iodide (0.02 g, 0.11 mmol) were added into a reaction vessel. Anhydrous DMF (20 mL) was then added. The temperature was raised to 80° C., and reaction was conducted for 13 hours. DMF was removed under reduced pressure. Washing was conducted using ethyl acetate and saturated sodium carbonate solution. Suction filtration was then conducted to obtain solid and filtrate, which were then respectively washed with substantial amounts of ethyl acetate and saturated sodium carbonate solution. An organic layer of each of the filtrates was collected. Solvent was removed from the organic layer under reduced pressure. Column chromatography was conducted using ethyl acetate:hexane=1:2 as eluent to obtain a white solid (0.119 g, 0.27 mmol, yield: 46.5%).

Spectral analysis data of the white solid: $^1$H NMR (400 MHz, CDCl$_3$, 298K), δ (ppm): 9.28 (d, J$_{HH}$=1.6 Hz, 1H), 9.17 (s, H), 9.03 (d, J$_{HH}$=1.6 Hz, 1H), 8.88 (dd, J$_{HH}$=4, 0.8 Hz, 1H), 8.80 (d, J$_{HH}$=8.8 Hz, 1H), 8.35 (d, J$_{HH}$=8.4 Hz, 1H), 8.24 (d, J$_{HH}$=8.4, 1.6 Hz, 1H), 7.91 (dd, J$_{HH}$=3.2, 1.6 Hz, 1H), 7.89 (d, J$_{HH}$=8.4, 1H), 7.76 (t, J$_{HH}$=7.2 Hz, 1H), 7.58 (t, J$_{HH}$=7.2 Hz, 1H), 4.50 (m, 4H), 1.47 (m, 6H). The chemical structure of the white solid was confirmed to be

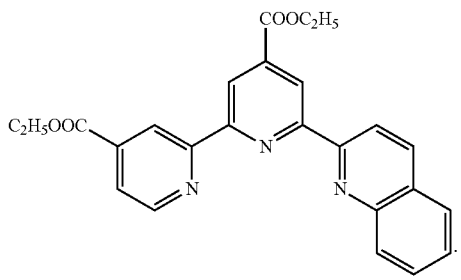

Synthesis Example 7

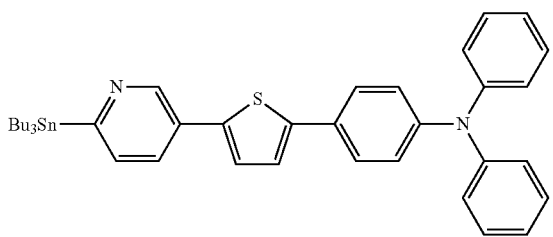

(2.02 g, 2.91 mmol), the product obtained in Preparation Example 1 (0.83 g, 2.189 mmol), and Pd(PPh$_3$)$_4$ (0.26 g, 0.2 mmol) were added into a 150 ml two-necked flask, which was then purged with nitrogen three times. Anhydrous DMF was added. The temperature was raised to 80° C., and reaction was conducted for 12 hours. Solvent was removed under reduced pressure. Dissolution was conducted using CH$_2$Cl$_2$. Extraction was then conducted using saline solution. An organic layer was obtained. Solvent was removed from the organic layer under reduced pressure. Column chromatography was conducted using CH$_2$Cl$_2$ as eluent to obtain a yellow solid (yield: 54%).

Spectral analysis data of the yellow solid: $^1$H NMR (400 MHz, CDCl$_3$, 298K), δ (ppm): 9.11 (s, 1H), 9.01 (d, J$_{HH}$=4.0 Hz, 1H), 8.99 (d, J$_{HH}$=4.0 Hz, 1H), 8.95 (d, J$_{HH}$=4.0 Hz, 1H), 8.88 (d, J$_{HH}$=4.0 Hz, 1H), 8.68 (d, J$_{HH}$=8.0 Hz, 1H), 8.10 (d, J$_{HH}$=8.0 Hz, 1H), 7.91 (d, J$_{HH}$=8.0 Hz, 1H), 7.53 (d, J$_{HH}$=8.0 Hz, 2H), 7.48 (d, J$_{HH}$=4.0 Hz, 1H), 7.27~7.31 (m, 5H), 7.04~7.13 (m, 8H), 4.45~4.51 (m, 4H), 1.25~1.49 (m, 6H). The chemical structure of the yellow solid was confirmed to be

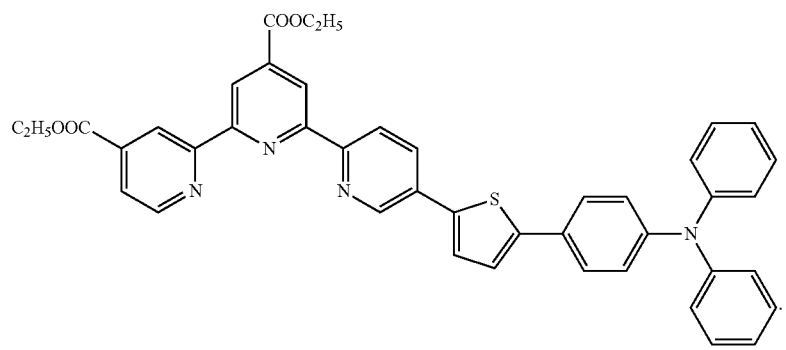

Synthesis Example 8

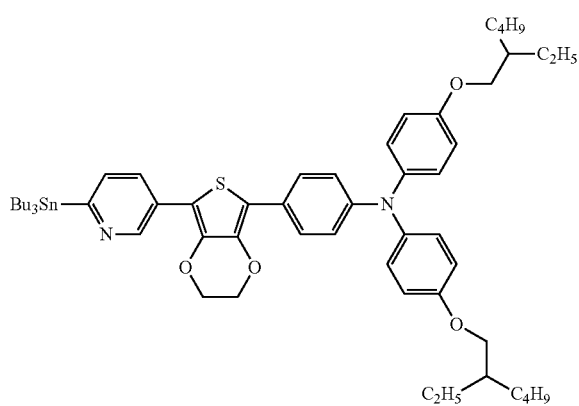

(2.98 g, 2.95 mmol), the product obtained in Preparation Example 1 (0.83 g, 2.189 mmol), and Pd(PPh$_3$)$_4$ (0.26 g, 0.2 mmol) were added into a 150 mL two-necked flask, which was then purged with nitrogen three times. Anhydrous DMF was added. The temperature was raised to 80° C., and reaction was conducted for 12 hours. Solvent was removed under reduced pressure. Dissolution was conducted by adding CH$_2$Cl$_2$. Extraction was then conducted by adding saline solution. An organic layer was obtained. Solvent was removed from the organic layer under reduced pressure. Column chromatography was conducted using CH$_2$Cl$_2$ as eluent, followed by recrystallization using CH$_2$Cl$_2$/hexane to obtain a yellow solid (0.78 g, yield: 35%).

Spectral analysis data of the yellow solid: $^1$H NMR (400 MHz, CDCl$_3$, 298K), δ (ppm): 9.12 (d, J$_{HH}$=2.4 Hz, 2H), 9.03 (s, 1H), 8.94 (s, 1H), 8.86 (d, J$_{HH}$=8.0 Hz, 1H), 8.62 (d, J$_{HH}$=8.0 Hz, 1H), 8.16 (d, J$_{HH}$=8.0 Hz, 1H), 7.89 (d, J$_{HH}$=4.8 Hz, 1H), 7.54 (d, J$_{HH}$=8.8 Hz, 2H), 7.09 (d, J$_{HH}$=8.8 Hz, 4H), 6.92 (d, J$_{HH}$=8.8 Hz, 2H), 6.81 (d, J$_{HH}$=8.8 Hz, 4H), 4.51~4.35 (m, 8H), 3.80 (d, J$_{HH}$=5.6 Hz, 4H) 1.68 (m, 2H), 0.8~1.54 (m, 34H). The chemical structure of the yellow solid was confirmed to be

Synthesis Example 9

The product obtained in Preparation Example 7 (1.1 g, 2.05 mmol), the product obtained in Preparation Example 1 (0.6 g, 1.58 mmol), PdCl$_2$ (0.011 g, 0.06 mmol), CuI (0.025 g, 0.13 mmol), and CsF (0.48 g, 3.16 mmol) were added into a 25 mL two-necked flask. Vacuuming and then filling of nitrogen were repeated three times. Anhydrous DMF (10 mL) was added. PBu$'_3$ (0.35 mL, 0.13 mmol, 10 wt %, dissolved in hexane) was then added. The temperature was raised to 80° C., and reaction was conducted for 24 hours. Reaction was ceased by adding deionized water (about 1 mL). Solvent was removed under vacuum. Methylene chloride was then added, and washing was conducted with water. An organic layer was collected and dehydrated using anhydrous magnesium sulfate. Filtrate was obtained via filtration, and was concentrated to remove solvent. Column chromatography was conducted using ethyl acetate:hexane=1:7 as eluent to obtain a white solid (0.438 g, yield: 51%).

Spectral analysis data of the white solid: $^1$H NMR (400 MHz, CDCl$_3$, 298K), δ (ppm): 9.14 (s, 1H), 9.11 (s, 1H), 8.96 (d, J$_{HH}$=1.2 Hz, 1H), 8.86 (d, J$_{HH}$=4.8 Hz, 1H), 8.46 (d, J$_{HH}$=7.6 Hz, 1H), 7.89 (d, J$_{HH}$=4.8 Hz, 1H), 7.84 (t, J$_{HH}$=8 Hz, 1H), 7.64 (d, J$_{HH}$=7.6 Hz, 1H), 7.49 (d, J$_{HH}$=3.6 Hz, 1H), 6.8 (d, J$_{HH}$=3.6 Hz, 1H), 4.52~4.45 (m, 4H), 2.85 (d, J$_{HH}$=7.6 Hz, 2H), 1.72~1.74 (m, 2H), 1.48~1.31 (m, 12H), 0.87~0.85 (m, 3H). The chemical structure of the white solid was confirmed to be

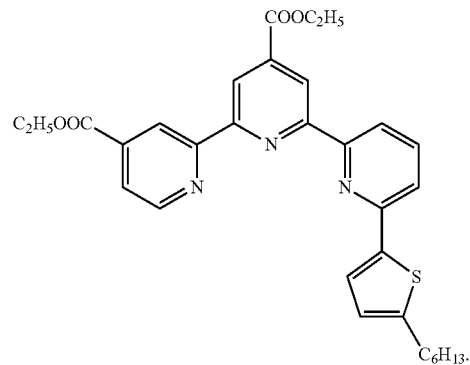

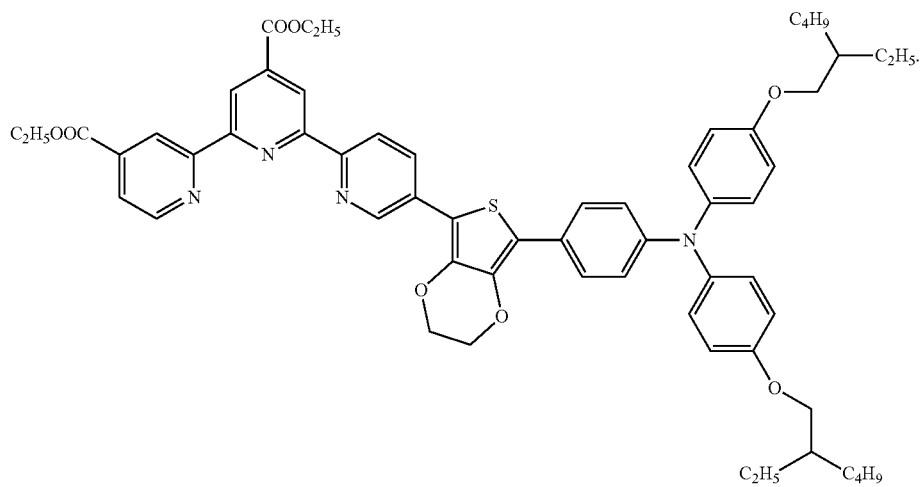

Synthesis Example 10

The product obtained in Preparation Example 8 (0.806 g, 1.36 mmol), the product obtained in Preparation Example 1 (0.428 g, 1.13 mmol), $PdCl_2$ (0.008 g, 0.045 mmol), CuI (0.017 g, 0.09 mmol), and CsF (0.343 g, 2.26 mmol) were added into a 25 ml two-necked flask. Vacuuming and then filling of nitrogen were repeated three times. Anhydrous DMF (10 mL) was added. $PBu^t_3$ (0.35 mL, 0.13 mmol, 10 wt %, dissolved in hexane) was then added. The temperature was raised to 80° C., and reaction was conducted for 24 hours. Reaction was ceased by adding deionized water (about 1 ml). Solvent was removed under vacuum. Methylene chloride was then added, and washing was conducted with water. An organic layer was collected and dehydrated using anhydrous magnesium sulfate. Filtrate was obtained via filtration, and was concentrated to remove solvent. Column chromatography was conducted using ethyl acetate:hexane=1:3 as eluent to obtain a white solid (0.346 g, yield: 42.2%).

Spectral analysis data of the white solid: $^1H$ NMR (400 MHz, $CDCl_3$, 298K), δ (ppm): 9.11 (s, 1H), 9.09 (s, 1H), 8.94 (d, $J_{HH}$=0.8 Hz, 1H), 8.86 (d, $J_{HH}$=5.2 Hz, 1H), 8.38 (d, $J_{HH}$=8 Hz, 1H), 7.93~7.88 (m, 2H) 7.81 (t, $J_{HH}$=8 Hz, 1H), 4.51~4.44 (m, 4H), 4.36~4.34 (m, 2H), 4.26~4.25 (m, 2H), 2.68 (t, $J_{HH}$=7.6 Hz, 2H,) 1.64~0.87 (m, 17H). The chemical structure of the white solid was confirmed to be

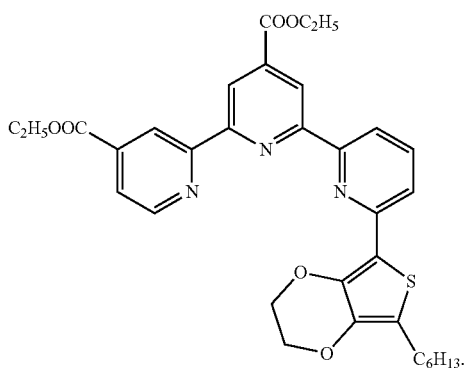

Preparation of Ruthenium Complex

Example 1

The product obtained in Synthesis Example 1 (0.261 g, 0.48 mmol) and $Ru(III)Cl_3 \cdot H_2O$ (0.127 g, 0.48 mmol) were added into a 50 ml one-necked flask. Anhydrous ethanol was then added, and heating was conducted for 6 hours under reflux. Temperature was reduced to room temperature. Precipitate was obtained via filtration and was washed using ice cold ethanol to obtain a dark brown solid (0.338 g).

The dark brown solid (0.338 g, 0.46 mmol) and tetrabutylammonium thiocyanate (0.980 g, 3.26 mmol) were added into a 150 ml one-necked flask. Deionized water (6 mL) was added, followed by DMF (30 mL). The one-necked flask was covered with aluminum foil and was heated for 6 hours under reflux. Temperature was reduced to room temperature. Solvent was removed by heating under vacuum. Column chromatography was conducted using ethyl acetate:methylene chloride=1:10 as eluent to obtain a dark green solid (0.170 g, yield: 36%).

The dark green solid (0.170 g, 0.16 mmol) was added into a 50 ml one-necked flask, and was dissolved by adding acetone. Tetrabutylammonium hydroxide (referred to as TBAOH hereinafter, 0.80 mL, 0.80 mmol) was added. Heating was conducted for 3 hours under reflux. Temperature was reduced to room temperature. Solvent was removed under reduced pressure. Deionized water (10 mL) was then added. An aqueous hydrogen chloride solution (2N) was added slowly until the pH value of 2 was reached. Precipitate was collected via centrifugation, and was washed using ethyl ether and deionized water to obtain a ruthenium complex (referred to as complex A-1 hereinafter, 0.016 g, yield: 94.5%).

Spectral analysis data of the complex A-1: $^1H$ NMR (400 MHz, $CD_3OD$, 298K), δ (ppm): 9.18 (s, 1H) 9.16 (d, $J_{HH}$=4.0 Hz, 1H), 8.88 (s, 2H), 8.81 (s, 1H), 8.62 (s, 1H), 8.31 (d, $J_{HH}$=8.0 Hz, 1H), 8.18 (d, $J_{HH}$=8.0 Hz, 1H), 8.08 (d, $J_{HH}$=12.0 Hz, 1H), 7.58 (d, $J_{HH}$=4.0 Hz, 1H), 6.92 (d, $J_{HH}$=4.0 Hz, 1H), 3.23 (m, 8H), 2.90 (t, $J_{HH}$=8.0 Hz, 2H), 1.75 (m, 2H), 1.65 (m, 8H), 0.81~1.46 (m, 29H). The chemical structure of the complex A-1 is shown in Table 1.

Example 2

The product obtained in Synthesis Example 2 (0.1 g, 0.16 mmol) and $Ru(III)Cl_3 \cdot H_2O$ (0.05 g, 0.16 mmol) were added into a 50 mL one-necked flask. Anhydrous ethanol was then added, and heating was conducted for 4 hours under reflux. Temperature was reduced to room temperature. Precipitate was obtained via filtration and was washed using ice cold ethanol to obtain a dark brown solid (0.14 g).

The dark brown solid (0.14 g, 0.17 mmol) and tetrabutylammonium thiocyanate (0.32 g, 1.02 mmol) were added into a 100 ml one-necked flask. Deionized water (3 ml) was added, followed by DMF (30 mL). The one-necked flask was covered with aluminum foil and was heated for 6 hours under reflux. Temperature was reduced to room temperature. Solvent was removed by heating under vacuum. Column chromatography was conducted using ethyl acetate:$CH_2Cl_2$=1:7 as eluent to obtain a dark green solid (0.6 g, yield: 32.5%).

The dark green solid (0.060 g, 0.054 mmol) was added into a 50 ml one-necked flask, and was dissolved by adding acetone. TBAOH (0.1 mL, 0.1 mmol) was added. Heating was conducted for 3 hours under reflux. Temperature was reduced to room temperature. Solvent was removed under reduced pressure. Deionized water (10 mL) was then added. An aqueous hydrogen chloride solution (2N) was added slowly until the pH value of 2 was reached. Precipitate was collected via centrifugation, and was washed using ethyl ether and deionized water to obtain a ruthenium complex (referred to as complex A-2 hereinafter, 0.04 g, yield: 70.18%).

Spectral analysis data of the complex A-2: $^1H$ NMR (400 MHz, $CD_3OD$, 298K), δ (ppm): 9.60 (d, $J_{HH}$=4.0 Hz, 1H), 9.17 (d, $J_{HH}$=8.0 Hz, 1H), 8.86 (s, 1H), 8.77 (s, 1H), 8.51 (s, 1H), 8.12~8.18 (m, 2H), 7.88 (d, $J_{HH}$=8.0 Hz, 1H), 4.70 (t, $J_{HH}$=8.0 Hz, 2H), 4.36 (t, $J_{HH}$=8.0 Hz, 2H), 3.21 (m, 8H), 2.72 (t, $J_{HH}$=8.0 Hz, 2H), 0.91~1.65 (m, 39H). The chemical structure of the complex A-2 is shown in Table 1.

Example 3

The product obtained in Synthesis Example 3 (0.08 g, 0.19 mmol) and $Ru(III)Cl_3 \cdot H_2O$ (0.049 g, 0.19 mmol) were added into a reaction vessel. Ethanol (30 mL) was then added. Temperature was raised to 80° C., and reflux was conducted for 4 hours. Temperature was reduced to room temperature. Reddish brown solid was collected via filtration under reduced pressure.

The reddish brown solid (0.095 g, 0.15 mmol),

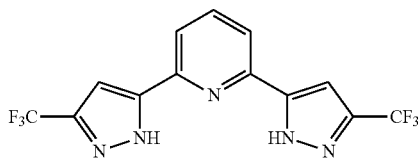 [SMILES: FC(F)(F)c1cc(-c2cccc(-c3cc(C(F)(F)F)n[nH]3)n2)[nH]n1]

(0.052 g, 0.15 mmol), and 4-ethylmorpholine (0.05 mL, 0.39 mmol) were added into a reaction vessel. Ethanol (30 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.8 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, $CH_2Cl_2$, and acetone sequentially to obtain a ruthenium complex (referred to as complex A-3 hereinafter, 0.105 g, 0.13 mmol, yield: 86%).

Spectral analysis data of the complex A-3: $^1$H NMR (400 MHz, $d_6$-DMSO, 298K), δ (ppm): 9.22 (s, 1H), 9.01 (s, 1H), 8.87 (s, 1H), 8.85 (s, 1H), 8.36 (d, $J_{HH}$=8.2 Hz, 1H), 8.23 (d, $J_{HH}$=8.1 Hz, 1H), 8.14 (t, $J_{HH}$=7.8 Hz, 1H), 7.97 (m, 3H), 7.78 (dd, $J_{HH}$=5.3, 1.3 Hz, 1H), 7.65 (dd, $J_{HH}$=6.4, 1.2 Hz, 1H), 7.43 (d, $J_{HH}$=5.9 Hz, 1H), 7.26 (dd, $J_{HH}$=8.2, 5.4 Hz, 1H), 7.17 (s, 2H). The chemical structure of the complex A-3 is shown in Table 1.

Example 4

The product obtained in Synthesis Example 3 (0.08 g, 0.19 mmol) and Ru(III)$Cl_3$·$H_2O$ (0.049 g, 0.19 mmol) were added into a reaction vessel. Ethanol (30 mL) was then added. Temperature was raised to 80° C., and reflux was conducted for 4 hours. Temperature was reduced to room temperature. Reddish brown solid was collected via filtration under reduced pressure.

The reddish brown solid (0.062 g, 0.10 mmol),

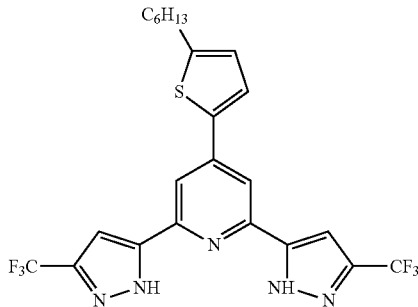

(0.050 g, 0.10 mmol), and 4-ethylmorpholine (0.03 mL, 0.25 mmol) were added into a reaction vessel. Ethanol (35 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.2 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, $CH_2Cl_2$, and acetone sequentially to obtain a ruthenium complex (referred to as complex A-4 hereinafter, 0.069 g, 0.07 mmol, yield: 71%).

Spectral analysis data of the complex A-4: $^1$H NMR (400 MHz, $d_6$-DMSO, 298K), δ (ppm): 9.22 (s, 1H), 9.01 (s, 1H), 8.89 (s, 1H), 8.87 (s, 1H), 8.36 (d, $J_{HH}$=7.4 Hz, 1H), 8.26 (s, 2H), 8.23 (s, 1H), 7.9 (m, 2H), 7.87 (dd, $J_{HH}$=5.3, 1.3 Hz, 1H), 7.67 (dd, $J_{HH}$=5.9, 1.5 Hz, 1H), 7.55 (d, $J_{HH}$=7.8 Hz, 1H), 7.31 (m, 3H), 7.11 (s, 1H), 2.96 (t, $J_{HH}$=7.4 Hz, 2H), 1.74 (m, 2H), 1.38 (m, 6H), 0.90 (t, $J_{HH}$=7.2 Hz, 3H). The chemical structure of the complex A-4 is shown in Table 1.

Example 5

The product obtained in Synthesis Example 3 (0.08 g, 0.19 mmol) and Ru(III)$Cl_3$·$H_2O$ (0.049 g, 0.19 mmol) were added into a reaction vessel. Ethanol (30 mL) was then added. Temperature was raised to 80° C., and reflux was conducted for 4 hours. Temperature was reduced to room temperature. Reddish brown solid was collected via filtration under reduced pressure.

The reddish brown solid (0.056 g, 0.09 mmol),

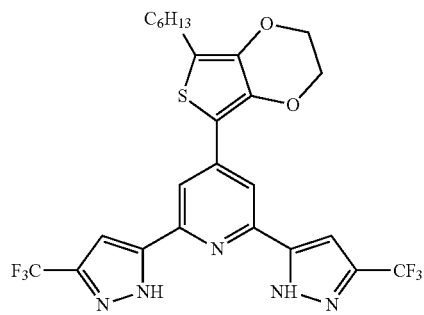

(0.050 g, 0.09 mmol), and 4-ethylmorpholine (0.03 mL, 0.23 mmol) were added into a reaction vessel. Ethanol (30 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.3 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, $CH_2Cl_2$, and acetone sequentially to obtain a ruthenium complex (referred to as complex A-5 hereinafter, 0.063 g, 0.06 mmol, yield: 70%).

Spectral analysis data of the complex A-5: $^1$H NMR (400 MHz, $d_6$-DMSO, 298K), δ (ppm): 9.22 (s, 1H), 9.02 (s, 1H), 8.89 (s, 1H), 8.87 (s, 1H), 8.37 (d, $J_{HH}$=7.2 Hz, 1H), 8.23 (d, $J_{HH}$=7.2 Hz, 1H), 8.18 (s, 2H), 7.98 (t, $J_{HH}$=8.0 Hz, 1H), 7.86 (dd, $J_{HH}$=5.2, 1.2 Hz, 1H), 7.68 (dd, $J_{HH}$=6.0, 2.0 Hz, 1H), 7.55 (d, $J_{HH}$=6.0 Hz, 1H), 7.31 (dd, $J_{HH}$=8.0, 5.2 Hz, 3H), 4.52 (s, 1H), 4.37 (s, 1H), 2.77 (t, $J_{HH}$=7.6 Hz, 2H), 1.63 (m, 2H), 1.32 (m, 6H), 0.89 (t, $J_{HH}$=6.8 Hz, 3H). The chemical structure of the complex A-5 is shown in Table 1.

Example 6

The product obtained in Synthesis Example 4 (0.05 g, 0.11 mmol) and Ru(III)Cl$_3$.H$_2$O (0.03 g, 0.11 mmol) were added into a reaction vessel. Ethanol (30 mL) was then added. Temperature was raised to 80° C., and reflux was conducted for 4 hours. Temperature was reduced to room temperature. A solid was collected via filtration under reduced pressure.

The solid (0.073 g, 0.11 mmol),

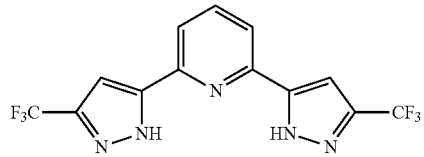 [SMILES: FC(F)(F)c1cc(-c2cccc(-c3cc(C(F)(F)F)n[nH]3)n2)[nH]n1]

(0.039 g, 0.11 mmol), and 4-ethylmorpholine (0.034 mL, 0.249 mmol) were added into a reaction vessel. Ethanol (25 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.9 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, methylene chloride, and acetone sequentially to obtain a ruthenium complex (referred to as complex A-6 hereinafter, 0.068 g, 0.096 mmol, yield: 87%).

Spectral analysis data of the complex A-6: $^1$H NMR (400 MHz, d$_6$-DMSO, 298K), δ (ppm): 9.20 (s, 1H), 8.99 (s, 1H), 8.90 (s, 1H), 8.72 (s, 1H), 8.22 (d, 7.9 Hz, 1H), 8.13 (t, $J_{HH}$=7.7 Hz, 1H), 7.95 (m, 4H), 7.72 (d, $J_{HH}$=4.6 Hz, 1H), 7.64 (d, $J_{HH}$=5.8, 1H), 7.41 (d, $J_{HH}$=5.9 Hz, 1H), 7.20 (dd, $J_{HH}$=7.4, 5.5 Hz, 1H), 7.15 (s, 1H), 2.67 (s, 3H). The chemical structure of the complex A-6 is shown in Table 1.

Example 7

The product obtained in Synthesis Example 5 (0.1 g, 0.22 mmol) and Ru(III)Cl$_3$.H$_2$O (0.059 g, 0.22 mmol) were added into a reaction vessel. Ethanol (30 mL) was then added. Temperature was raised to 80° C., and reflux was conducted for 4 hours. Temperature was reduced to room temperature. A solid was collected via filtration under reduced pressure.

The solid (0.06 g, 0.09 mmol),

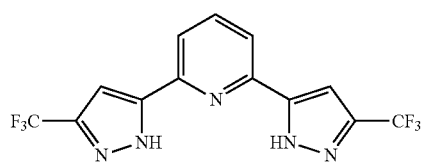 [SMILES: FC(F)(F)c1cc(-c2cccc(-c3cc(C(F)(F)F)n[nH]3)n2)[nH]n1]

(0.032 g, 0.09 mmol), and 4-ethylmorpholine (0.03 mL, 0.24 mmol) were added into a reaction vessel. Ethanol (30 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.5 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, methylene chloride, and acetone sequentially to obtain a ruthenium complex (referred to as complex A-7 hereinafter, 0.087 g, 0.10 mmol, yield: 93%).

Spectral analysis data of the complex A-7: $^1$H NMR (400 MHz, d$_6$-DMSO, 298K), δ (ppm): 9.26 (s, 1H), 9.04 (s, 1H), 8.91 (s, 1H), 8.82 (dd, $J_{HH}$=10.4, 2.8 Hz, 1H), 8.30 (d, $J_{HH}$=8.0 Hz, 1H), 8.16 (t, $J_{HH}$=8.0 Hz, 1H), 8.08 (dd, $J_{HH}$=7.6, 2.8 Hz, 1H), 8.00 (d, $J_{HH}$ 8.0 Hz, 2H), 7.75 (d, $J_{HH}$=4.4, 1H), 7.66 (dd, $J_{HH}$=6.0, 1.6 Hz, 1H), 7.42 (d, $J_{HH}$=6.0 Hz, 1H), 7.28 (dd, $J_{HH}$=8.0, 5.2 Hz, 1H), 7.22 (s, 2H); $^{19}$F-NMR (376 MHz, d$_6$-DMSO, 298K), δ (ppm): ~58.64 (s, 6F; CF$_3$), ~112.41 (s, 1F). The chemical structure of the complex A-7 is shown in Table 1.

Example 8

The product obtained in Synthesis Example 6 (0.080 g, 0.19 mmol) and Ru (III) Cl$_3$.H$_2$O (0.049 g, 0.19 mmol) were added into a reaction vessel. Ethanol (30 mL) was then added. Temperature was raised to 80° C., and reflux was conducted for 4 hours. Temperature was reduced to room temperature. Reddish brown solid was collected via filtration under reduced pressure.

The reddish brown solid (0.095 g, 0.15 mmol),

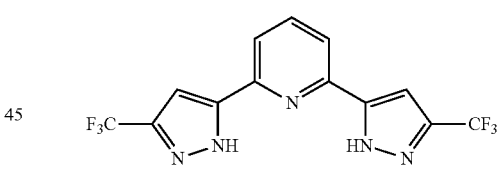

(0.052 g, 0.15 mmol), and 4-ethylmorpholine (0.05 mL, 0.39 mmol) were added into a reaction vessel. Ethanol (30 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.8 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, methylene chloride, and acetone sequentially to obtain a ruthenium complex (referred to as complex A-8 hereinafter, 0.105 g, 0.13 mmol, yield: 86%).

Spectral analysis data of the complex A-8: $^1$H NMR (400 MHz, d$_6$-DMSO, 298K), δ (ppm): 9.48 (s, 1H), 9.35 (s, 1H), 9.12 (s, 1H), 9.14 (s, 1H), 8.61 (d, $J_{HH}$=8.4 Hz, 1H), 8.34 (t, $J_{HH}$=7.6 Hz, 1H), 8.23 (d, $J_{HH}$=8 Hz, 2H), 7.99 (d, $J_{HH}$=8 Hz, 1H), 7.74 (d, $J_{HH}$=8 Hz, 1H), 7.54 (t, $J_{HH}$=7.6 Hz, 1H), 7.29 (m, 3H), 7.23 (d, $J_{HH}$=8 Hz, 1H), 7.17 (d, $J_{HH}$=8 Hz, 1H). The chemical structure of the complex A-8 is shown in Table 1.

Example 9

The product obtained in Synthesis Example 6 (0.080 g, 0.19 mmol) and Ru (III) Cl$_3$.H$_2$O (0.049 g, 0.19 mmol) were added into a reaction vessel. Ethanol (30 mL) was then added. Temperature was raised to 80° C., and reflux was conducted for 4 hours. Temperature was reduced to room temperature. Reddish brown solid was collected via filtration under reduced pressure.

The reddish brown solid (0.062 g, 0.10 mmol),

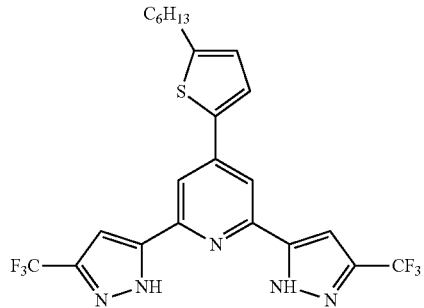

(0.050 g, 0.10 mmol), and 4-ethylmorpholine (0.03 mL, 0.25 mmol) were added into a reaction vessel. Ethanol (35 mL) was added. Temperature was raised to 80° C. and reaction was conducted for 4 hours. Ethanol was removed under reduced pressure. Column chromatography was conducted using ethyl acetate:hexane=1:1 as eluent to obtain a reddish black solid.

The reddish black solid was added into a mixture of aqueous sodium hydroxide solution (2.2 mL, 1.0 M) and acetone (30 mL). Temperature was raised to 60° C. and hydrolysis was conducted for 4 hours under reflux. Temperature was reduced to room temperature. An aqueous hydrogen chloride solution (2N) was added slowly until the pH value of 3 was reached to produce a black solid, which was collected and washed using water, CH$_2$Cl$_2$, and acetone sequentially to obtain a ruthenium complex (referred to as complex A-9 hereinafter, 0.065 g, 0.066 mmol, yield: 68%).

Spectral analysis data of the complex A-9: $^1$H NMR (400 MHz, d$_6$-DMSO, 298K), δ (ppm): 9.49 (s, 1H), 9.34 (s, 1H), 9.12 (d, $J_{HH}$=8.2 Hz, 1H), 9.09 (s, 1H), 8.62 (d, $J_{HH}$=8.2 Hz, 1H), 8.45 (d, $J_{HH}$=8.1 Hz, 1H), 8.05 (s, 1H), 8.00 (d, $J_{HH}$=8.1 Hz, 3H), 7.75 (s, 1H), 7.52 (s, H), 7.35 (s, 1H), 7.31 (s, 1H), 7.15 (s, 1H), 2.99 (t, $J_{HH}$=7.4 Hz, 2H), 1.76 (m, 2H), 1.35 (m, 6H), 0.90 (t, $J_{HH}$=7.2 Hz, 3H). The chemical structure of the complex A-9 is shown in Table 1.

Example 10

The product obtained in Synthesis Example 9 (0.175 g, 0.32 mmol) and RuCl$_3$.3H$_2$O (0.092 g, 0.35 mmol) were added into a 25 mL one-necked flask. Anhydrous ethanol (15 mL) was then added. Reflux was conducted for 4 hours under nitrogen. Temperature was reduced to room temperature. The flask stood still for 12 hours. Black brown solid (0.109 g, yield: 45.4%) was obtained after filtration under reduced pressure following by washing with ethanol several times.

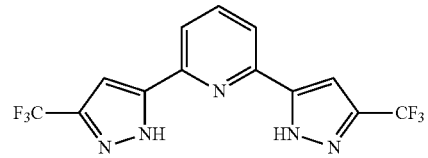 [SMILES: FC(F)(F)c1cc(-c2cccc(-c3cc(C(F)(F)F)n[nH]3)n2)[nH]n1]

(0.0461 g, 0.133 mmol), the black brown solid (0.100 g, 0.133 mmol), and 4-ethylmorpholine (0.04 mL, 0.345 mmol) were added into a 25 mL one-necked flask. Anhydrous ethanol (15 mL) was added. Reflux was conducted for 6 hours under nitrogen. Temperature was reduced to room temperature. Solvent was removed via rotary concentration. Methylene chloride was added. Contents in the flask were washed using water. An organic layer was collected, and water was removed using anhydrous magnesium sulfate. Filtrate was obtained via filtration, and was concentrated to remove solvent. Column chromatography was conducted using ethyl acetate:hexane=1:1 as eluent to obtain a black brown solid (0.117 g, yield: 88.9%).

The black brown solid was added into a 25 ml one-necked flask. Acetone (10 mL) and an aqueous sodium hydroxide solution (4 mL, 0.5 N) were added sequentially. Reflux was conducted for 4 hours. Temperature was then reduced to room temperature. Solvent was removed via rotary concentration. Water (10 mL) was added. An aqueous hydrogen chloride solution (2N) was added slowly until the pH value of 3 was reached to produce a solid, which was collected and washed using water, methylene chloride, and acetone sequentially to obtain a ruthenium complex (referred to as complex A-10 hereinafter, 0.099 g, yield: 90.1%).

Spectral analysis data of the complex A-10: $^1$H NMR (400 MHz, d$_6$-DMSO, 298K), δ (ppm): 9.21 (s, 1H), 9.15 (s, 1H), 8.99 (d, J=8 Hz, 1H), 8.97 (s, 1H), 7.96 (t, J=8 Hz, 1H), 7.89 (t, J=8 Hz, 1H), 7.73 (d, J=8 Hz, 1H), 7.62 (d, J=6 Hz, 1H), 7.32 (d, J=7.6 Hz, 1H), 7.11 (s, 2H), 6.78 (d, J=6 Hz, 1H), 6.11 (d, J=3.2 Hz, 1H), 5.38 (d, J=3.2 Hz, 1H), 2.57 (t, J=7.6 Hz, 2H), 1.50 (quin, J=7.6 Hz, 2H), 1.31 (m, 6H), 0.87 (t, J=6.8 Hz, 3H). $^{19}$F NMR (376 MHz, d$_6$-DMSO, 298K), δ (ppm): −38.30 (s, 6F). The chemical structure of the complex A-10 is shown in Table 1.

Example 11

The product obtained in Synthesis Example 10 (0.132 g, 0.22 mmol) and RuCl$_3$.3H$_2$O (0.063 g, 0.24 mmol) were added into a 25 mL one-necked flask. Anhydrous ethanol (15 mL) was then added. Reflux was conducted for 4 hours under nitrogen. Temperature was reduced to room temperature. The flask stood still for 12 hours. Black brown solid (0.156 g, yield: 88%) was obtained after filtration under reduced pressure following by washing with ethanol several times.

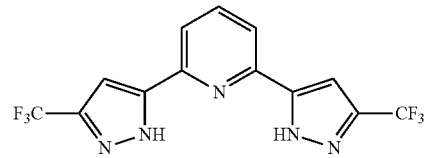 [SMILES: FC(F)(F)c1cc(-c2cccc(-c3cc(C(F)(F)F)n[nH]3)n2)[nH]n1]

(0.0461 g, 0.133 mmol), the black brown solid (0.1 g, 0.123 mmol), and 4-ethylmorpholine (0.04 mL, 0.32 mmol) were added into a 25 mL one-necked flask. Anhydrous ethanol (15 mL) was added. Reflux was conducted for 16 hours under nitrogen. Temperature was reduced to room temperature. Solvent was removed via rotary concentration. Methylene chloride was added. Contents in the flask were washed using water. An organic layer was collected, and water was removed using anhydrous magnesium sulfate. Filtrate was obtained via filtration, and was concentrated to remove solvent. Column chromatography was conducted using ethyl acetate:hexane=1:2, ethyl acetate:hexane=1:1, and ethyl acetate:hexane=2:1 sequentially as eluents to obtain a black brown solid (0.089 g, yield: 69%).

The black brown solid was added into a 25 mL one-necked flask. Acetone (10 mL) and an aqueous sodium hydroxide solution (4 mL, 0.5 N) were added sequentially. Reflux was conducted for 4 hours. Temperature was then reduced to room temperature. Solvent was removed via rotary concentration. Water (10 mL) was added. An aqueous hydrogen chloride solution (2N) was added slowly until the pH value of 3 was reached to produce a solid, which was collected and was washed using water, methylene chloride, and acetone sequentially to obtain a ruthenium complex (referred to as complex A-11 hereinafter, 0.0514 g, yield: 61.1%).

Spectral analysis data of the complex A-11: $^1$H NMR (400 MHz, $d_6$-DMSO, 298K), δ (ppm): 9.21 (s, 1H), 9.16 (s, 1H), 9.02 (d, J=5 Hz, 1H), 8.98 (s, 1H), 7.97 (q, J=7.2 Hz, 2H), 7.83 (m, 2H), 7.63 (d, J=4.8 Hz, 1H), 7.29 (d, J=7.2 Hz, 1H), 7.16 (s, 2H), 6.82 (d, J=6 Hz, 1H), 4.06 (s, 2H), 3.68 (s, 2H), 2.38 (m, 2H), 1.41~0.86 (m, 11H): $^{19}$F NMR (376 MHz, $d_6$-DMSO, 298K), δ (ppm): −58.24 (s, 6F). The chemical structure of the complex A-11 is shown in Table 1.

Example 12

The product obtained in Synthesis Example 7 (0.12 g, 0.20 mmol) and Ru (III) Cl$_3$.H$_2$O (0.05 g, 0.20 mmol) were added into a 50 mL one-necked flask. Ethanol was then added. Heating was conducted for 6 hours under reflux. Temperature was reduced to room temperature. Precipitate was obtained via filtration and was washed using ice cold ethanol to obtain a dark brown solid (0.18 g).

The dark brown solid (0.18 g, 0.55 mmol) and tetrabutylammonium thiocyanate (0.357 g, 1.18 mmol) were added into a 150 mL one-necked flask. Deionized water (0.4 mL) was added, followed by DMF (30 mL). The one-necked flask was covered with aluminum foil and was heated for 6 hours under reflux. Temperature was reduced to room temperature. Solvent was removed by heating under vacuum. Column chromatography was conducted using ethyl acetate:methylene chloride=1:7 as eluent to obtain a dark green solid (0.07 g, yield: 33%).

The dark green solid (0.07 g, 0.06 mmol) was added into a 50 ml one-necked flask, and was dissolved by adding acetone. TBAOH (0.3 mL, 0.3 mmol) was added. Heating was conducted for 3 hours under reflux. Temperature was reduced to room temperature. Solvent was removed under reduced pressure. Deionized water (10 mL) was then added. An aqueous hydrogen chloride solution (2N) was added slowly until the pH value of 2 was reached. Precipitate was collected via centrifugation, and was washed using ethyl ether and deionized water to obtain a ruthenium complex (referred to as complex A-12 hereinafter, 0.045 g, yield: 67.5%).

Spectral analysis data of the complex A-12: $^1$H NMR (400 MHz, $d_6$-acetone, 298K), δ (ppm): 9.37 (d, $J_{HH}$=4.0 Hz, 1H), 9.24 (d, $J_{HH}$=8.0 Hz, 1H), 9.02 (s, 1H), 8.98 (s, 1H), 8.81 (s, 1H), 8.71 (d, $J_{HH}$=8.0 Hz, 1H), 8.29~8.34 (m, 2H), 7.85 (d, $J_{HH}$=4.0 Hz, 1H), 7.71 (s, 1H), 7.68 (s, 1H), 7.54 (d, $J_{HH}$=4.0 Hz, 1H), 7.32~7.36 (m, 4H), 7.06~7.15 (m, 8H), 3.42~3.45 (m, 8H), 1.81~1.92 (m, 8H), 1.40~1.44 (m, 8H), 1.00~0.86 (m, 12H). The chemical structure of the complex A-12 is shown in Table 1.

Example 13

The product obtained in Synthesis Example 8 (0.23 g, 0.23 mmol) and Ru(III)Cl$_3$.H$_2$O (0.06 g, 0.23 mmol) were added into a 50 mL one-necked flask. Ethanol was then added. Heating was conducted for 6 hours under reflux. Temperature was reduced to room temperature. Precipitate was obtained via filtration and was washed using ice cold ethanol to obtain a dark brown solid (0.3 g).

The dark brown solid (0.3 g, 0.25 mmol) and tetrabutylammonium thiocyanate (0.472 g, 1.57 mmol) were added into a 150 mL one-necked flask. Deionized water (0.45 mL) was added, followed by DMF (30 mL). The one-necked flask was covered with aluminum foil and was heated for 6 hours under reflux. Temperature was reduced to room temperature. Solvent was removed by heating under vacuum. Column chromatography was conducted using ethyl acetate:CH$_2$Cl$_2$=1:10 as eluent to obtain a dark green solid (0.098 g, yield: 31%).

The dark green solid (0.098 g, 0.063 mmol) was added into a 50 ml one-necked flask, and was dissolved by adding acetone. TBAOH (0.3 mL, 0.3 mmol) was added. Heating was conducted for 3 hours under reflux. Temperature was reduced to room temperature. Solvent was removed under reduced pressure. Deionized water (10 mL) was then added. An aqueous hydrogen chloride solution (2N) was added slowly until the pH value of 2 was reached. Precipitate was collected via centrifugation, and was washed using ethyl ether and deionized water to obtain a ruthenium complex (referred to as complex A-13 hereinafter, 0.09 g, yield: 94%).

Spectral analysis data of the complex A-13: $^1$H NMR (400 MHz, $d_6$-DMSO, 298K), δ (ppm): 9.55 (d, $J_{HH}$=2.0 Hz, 1H), 9.00~8.94 (m, 3H), 8.82 (s, 1H), 8.71 (d, $J_{HH}$=8.8 Hz, 1H), 8.19 (d, $J_{HH}$=6.4 Hz, 1H), 8.00 (d, $J_{HH}$=8.0 Hz, 1H), 7.58 (d, $J_{HH}$=8.8 Hz, 2H), 7.05 (d, $J_{HH}$=8.8 Hz, 4H), 6.92 (d, $J_{HH}$=8.8 Hz, 4H), 6.82 (d, $J_{HH}$=8.8 Hz, 2H), 4.74 (s, 2H), 4.48 (s, 2H), 3.83 (d, $J_{HH}$=5.6 Hz, 8H), 3.15 (m, 8H), 1.69~0.86 (m, 58H). The chemical structure of the complex A-13 is shown in Table 1.

Example 14

The product obtained in Synthesis Example 1 (0.15 g, 0.27 mmol) and Ru (III)Cl$_3$.H$_2$O (0.08 g, 0.30 mmol) were added into a 50 mL one-necked flask. Ethanol was then added. Reflux was conducted for 6 hours. Temperature was reduced to room temperature. Precipitate was obtained via filtration and was washed several times using ethanol to obtain a dark brown solid (0.17 g).

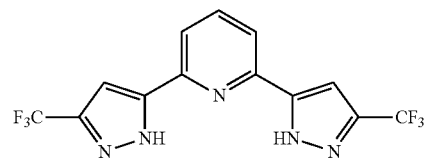 [SMILES: FC(F)(F)c1cc(-c2cccc(-c3cc(C(F)(F)F)n[nH]3)n2)[nH]n1]

(0.046 g, 0.13 mmol), the dark brown solid (0.1 g), and 4-ethylmorpholine (0.04 mL, 0.32 mmol) were added into a 25 mL one-necked flask. Anhydrous ethanol (15 mL) was added. Reflux was conducted for 6 hours under nitrogen. Temperature was reduced to room temperature. Solvent was removed via rotary concentration. Methylene chloride was added. Contents in the flask were washed using water. An organic layer was collected, and water was removed using anhydrous magnesium sulfate. Filtrate was obtained via filtration, and was concentrated to remove solvent. Column chromatography was conducted using ethyl acetate:hexane=1:3 and ethyl acetate:hexane=1:sequentially as eluents to obtain a black brown solid (0.055 g, yield: 41.7%).

The black brown solid was added into a 25 ml one-necked flask. Acetone (10 mL) and an aqueous sodium hydroxide solution (0.55 mL, 0.5 N) were added sequentially. Reflux was conducted for 4 hours. Temperature was then reduced to room temperature. Solvent was removed via rotary concentration. Water (10 mL) was added. An aqueous hydrogen chloride solution (2N) was added slowly until the pH value of 3 was reached to produce a solid, which was collected and washed using water, $CH_2Cl_2$, and acetone sequentially to obtain a ruthenium complex (referred to as complex A-14 hereinafter, 0.041 g, yield: 79.7%).

Spectral analysis data of the complex A-14: $^1$H NMR (400 MHz, $d_6$-DMSO, 298K), (ppm): 9.21 (s, 1H), 9.10 (s, 1H), 9.09 (s, 1H), 8.85 (d, $J_{HH}$=8 Hz, 1H), 8.23~8.05 (m, 4H), 7.69~7.63 (m, 2H), 7.28~7.20 (m, 4H), 6.81 (d, $J_{HH}$=3.2 Hz, 1H), 2.71 (t, $J_{HH}$=7.6 Hz, 2H), 1.52~0.82 (m, 11H). $^{19}$F NMR (376 MHz, $d_6$-DMSO, 298K): δ −58.48 (s, 6F). The chemical structure of the complex A-14 is shown in Table 1.

Example 15

The product obtained in Synthesis Example 2 (0.14 g, 0.23 mmol) and Ru(III)Cl$_3$.H$_2$O (0.06 g, 0.25 mmol) were added into a 50 mL one-necked flask. Ethanol was then added. Reflux was conducted for 6 hours. Temperature was reduced to room temperature. Precipitate was obtained via filtration and was washed several times using ethanol to obtain a dark brown solid (0.15 g).

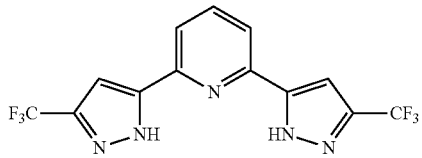 [SMILES: FC(F)(F)c1cc(-c2cccc(-c3cc(C(F)(F)F)n[nH]3)n2)[nH]n1]

(0.015 g, 0.18 mmol), the dark brown solid (0.064 g), and 4-ethylmorpholine (0.06 mL, 0.48 mmol) were added into a 25 mL one-necked flask. Anhydrous ethanol (15 mL) was added. Reflux was conducted for 6 hours under nitrogen. Temperature was reduced to room temperature. Solvent was removed via rotary concentration. Methylene chloride was added. Contents in the flask were washed using water. An organic layer was collected, and water was removed using anhydrous magnesium sulfate. Filtrate was obtained via filtration, and was concentrated to remove solvent. Column chromatography was conducted using ethyl acetate:hexane=1:3 and ethyl acetate:hexane=1:sequentially as eluents to obtain a black brown solid (0.083 g, yield: 43%).

The black brown solid was added into a 25 ml one-necked flask. Acetone (10 mL) and an aqueous sodium hydroxide solution (0.79 mL, 0.5 N) were added sequentially. Reflux was conducted for 4 hours. Temperature was then reduced to room temperature. Solvent was removed via rotary concentration. Water (10 mL) was added. An aqueous hydrogen chloride solution (2N) was added slowly until the pH value of 3 was reached to produce a solid, which was collected and washed using water, $CH_2Cl_2$, and acetone sequentially to obtain a ruthenium complex (referred to as complex A-15 hereinafter, 0.073 g, yield: 93%).

Spectral analysis data of the complex A-15: $^1$H NMR (400 MHz, CDCl$_3$, 298K), (ppm): 9.30 (s, 1H), 9.14 (s, 1H), 9.09 (s, 1H), 8.76 (d, $J_{HH}$=9.2 Hz, 1H), 8.20 (t, $J_{HH}$=8 Hz, 1H), 8.10 (s, 1H), 8.08 (s, 1H), 7.73 (m, 3H), 7.68 (d, $J_{HH}$=5.6 Hz, 1H), 7.26 (s, 1H), 4.16 (m, 2H), 4.10 (m, 2H), 2.54 (t, $J_{HH}$=8 Hz, 2H), 1.46~0.825 (m, 11H). The chemical structure of the complex A-15 is shown in Table 1.

Figure 2:
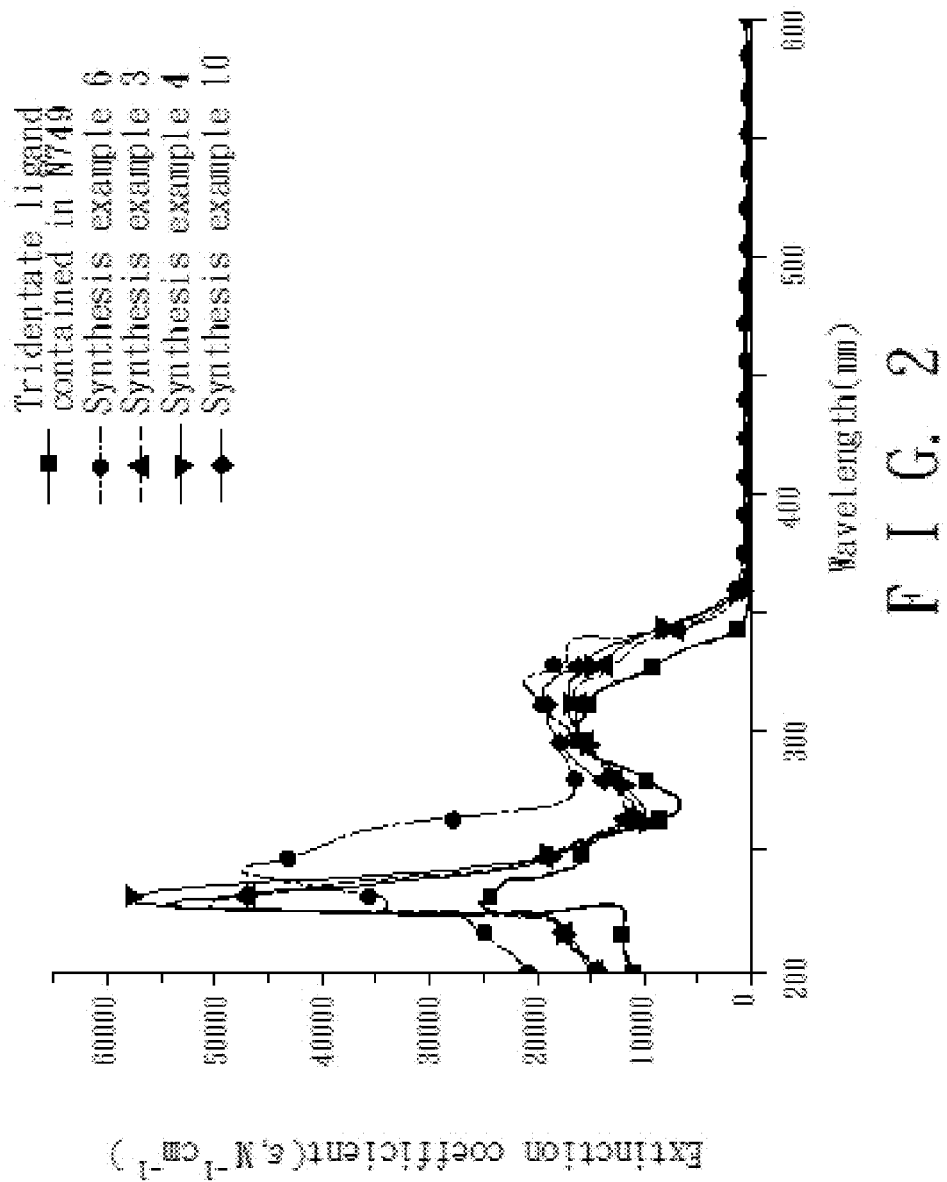
Figure 3:
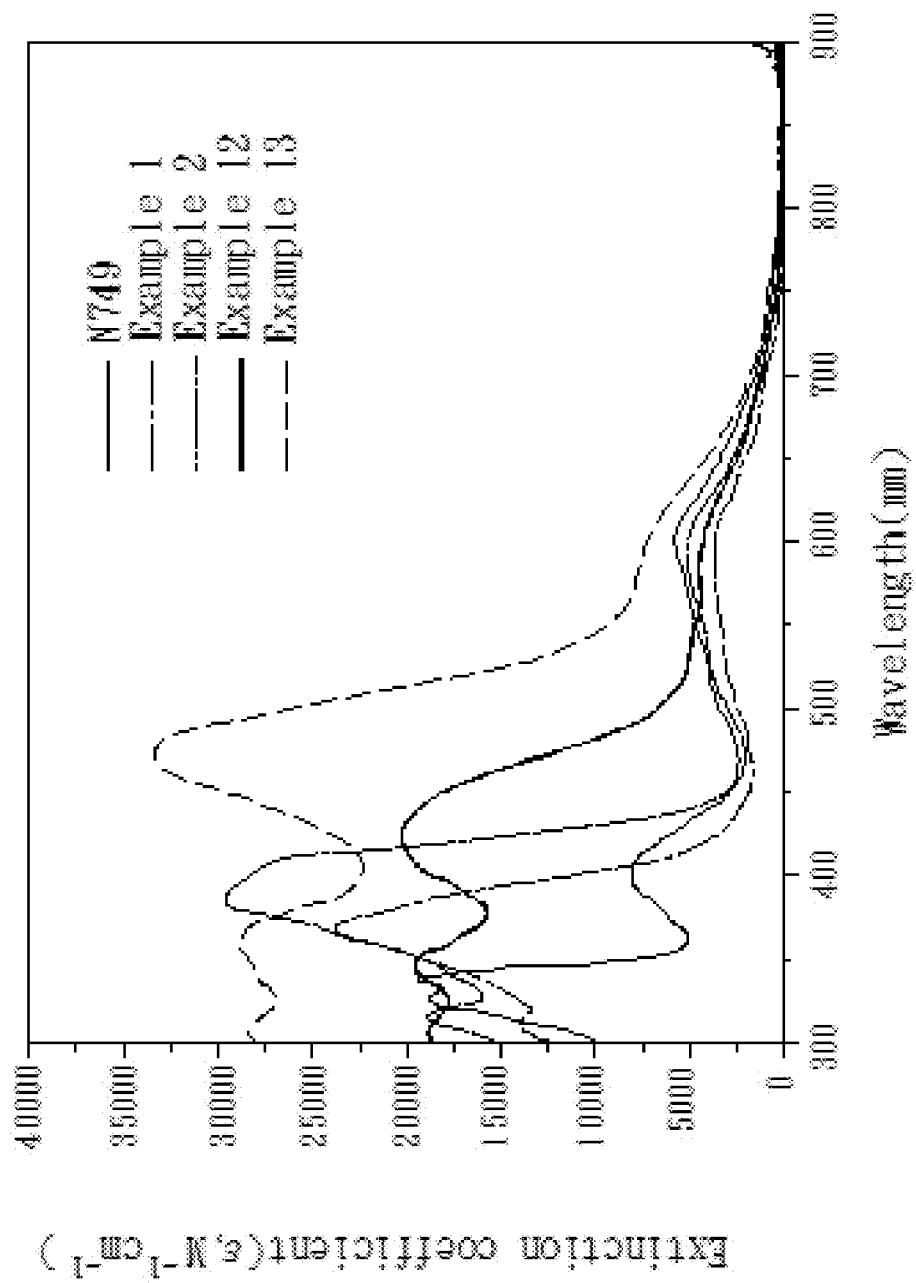
FIGS. 3 and 4 are graphs illustrating the absorption spectra of the examples of ruthenium complexes according to the present invention and conventional metal complexes.
Figure 4:
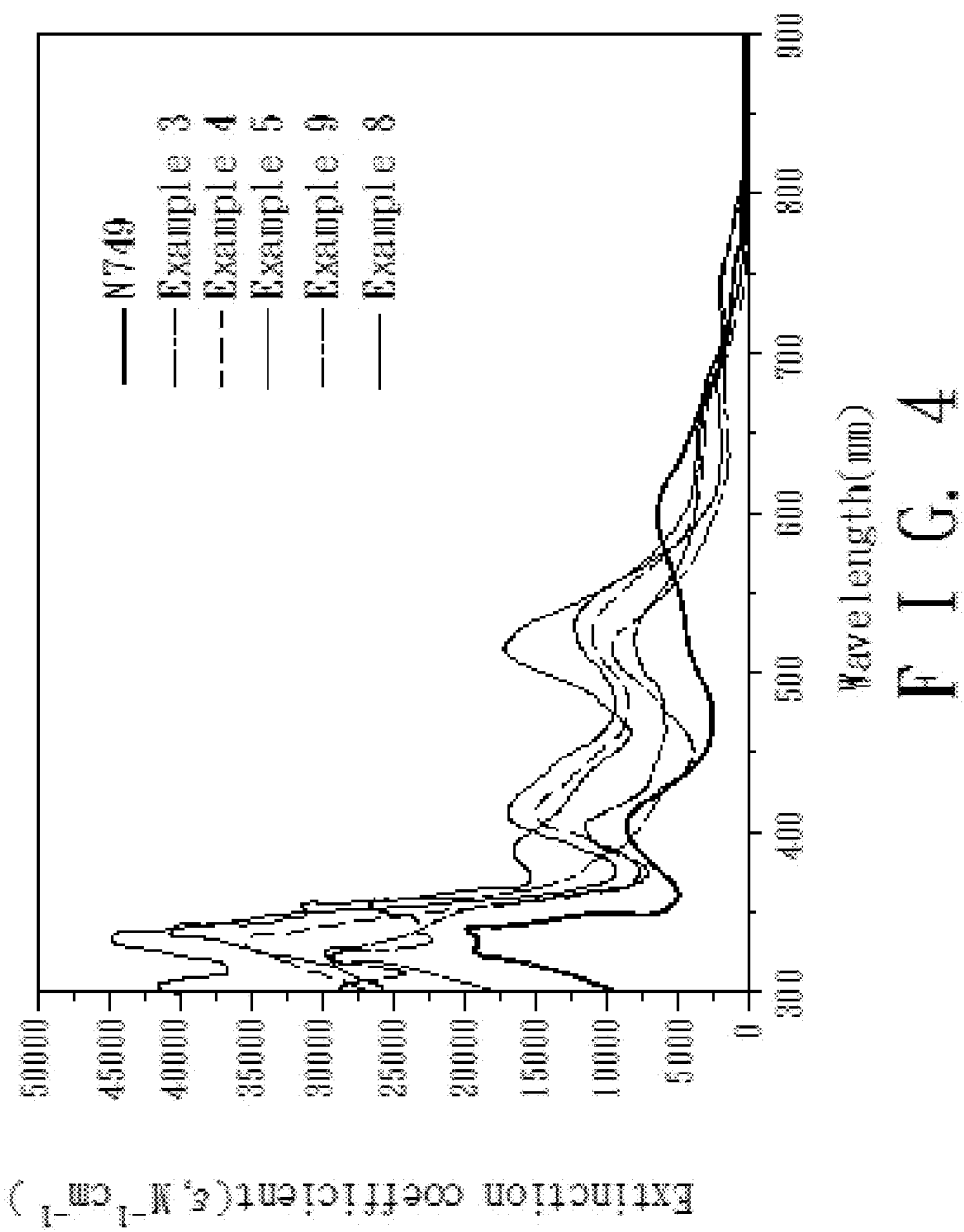

The absorption spectra of the examples of tridentate ligands according to the present invention and a conventional tridentate ligand are shown in FIGS. 1 and 2. The absorption spectra of the examples of ruthenium complexes according to the present invention and a conventional complex are shown in FIGS. 3 and 4. The result of an electrical property test is shown in Table 2.

TABLE 1

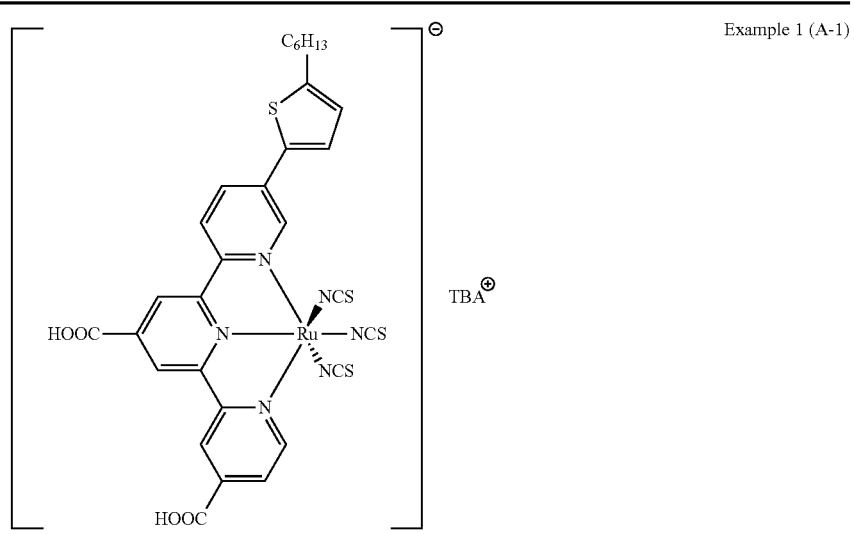

Example 1 (A-1)

TABLE 1-continued
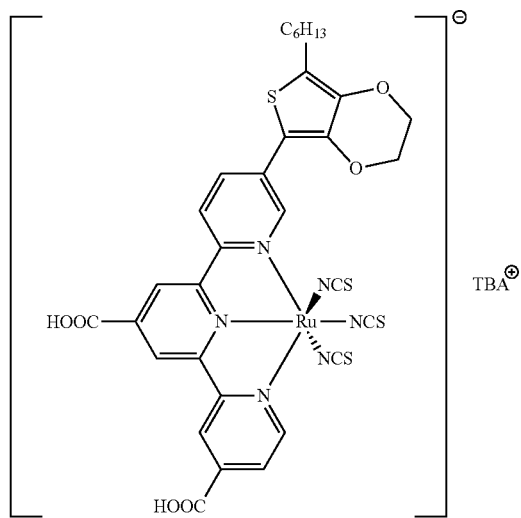 Example 2 (A-2)
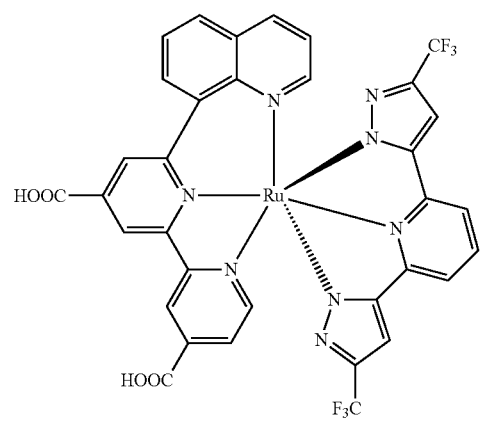 Example 3 (A-3)
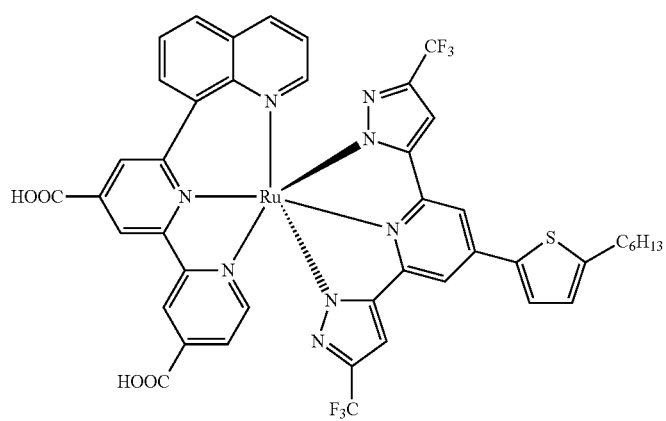 Example 4 (A-4)

TABLE 1-continued
| | |
|---|---|
| 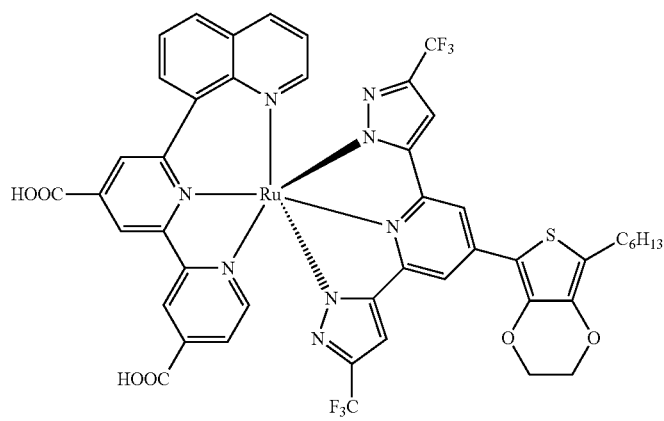 | Example 5 (A-5) |
| 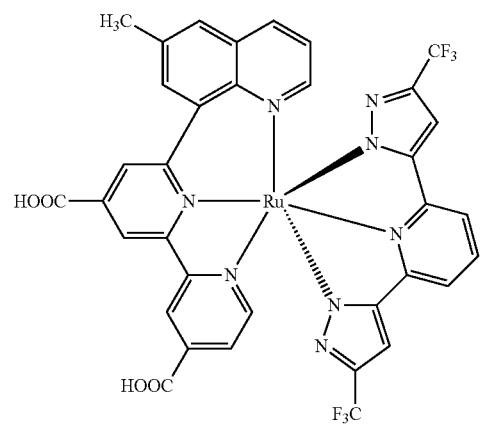 | Example 6 (A-6) |
| 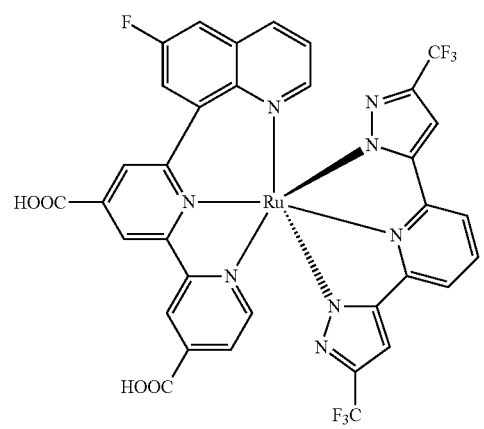 | Example 7 (A-7) |

TABLE 1-continued
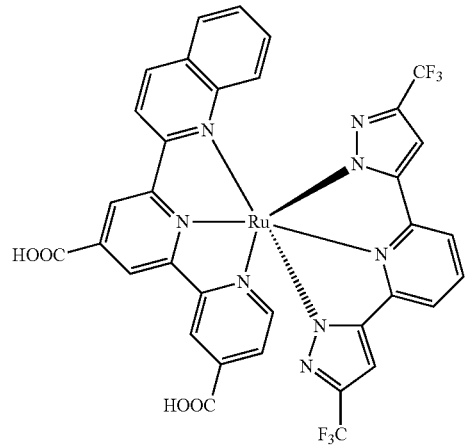
Example 8 (A-8)
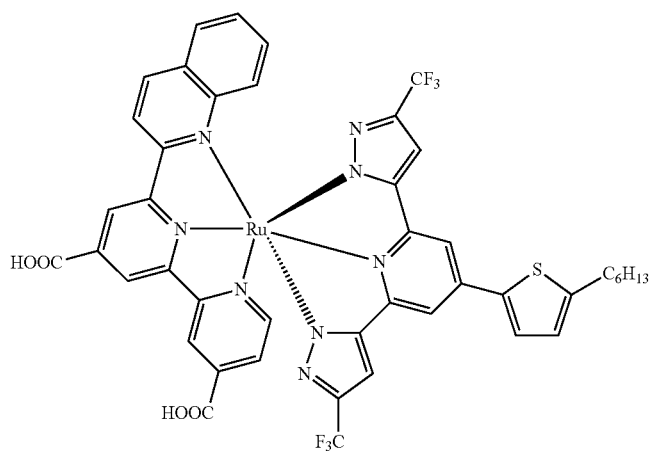
Example 9 (A-9)
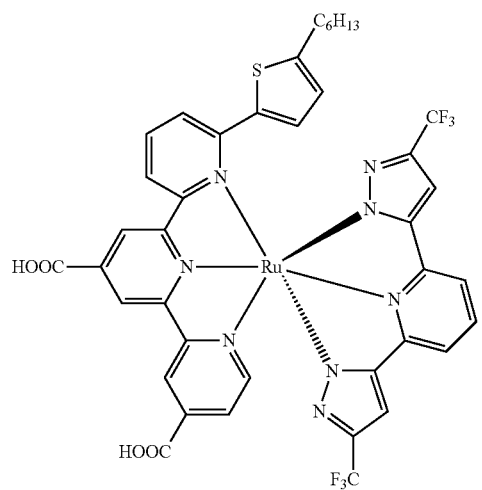
Example 10 (A-10)

TABLE 1-continued
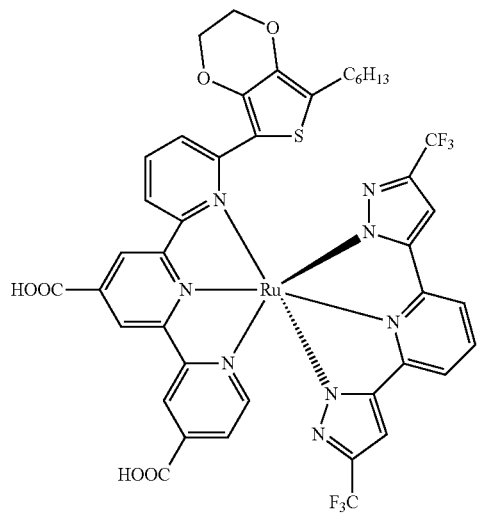
Example 11 (A-11)
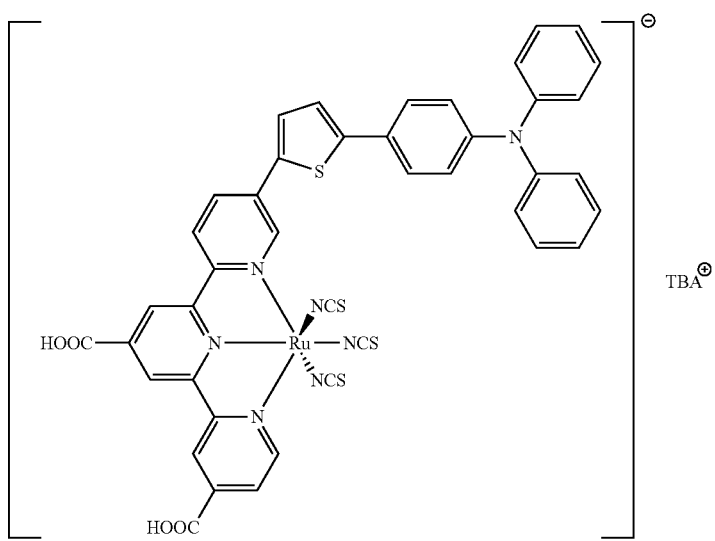
Example 12 (A-12)
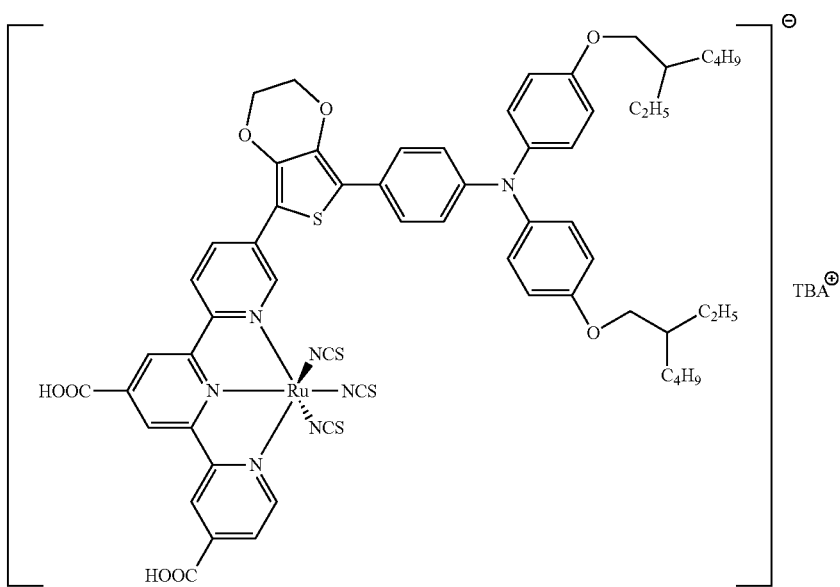
Example 13 (A-13)

TABLE 1-continued
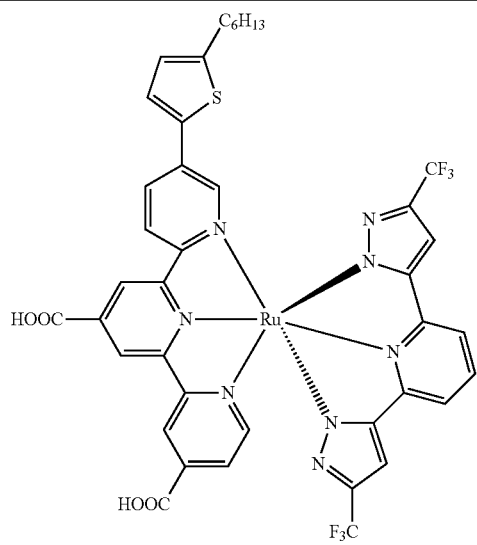
Example 14 (A-14)
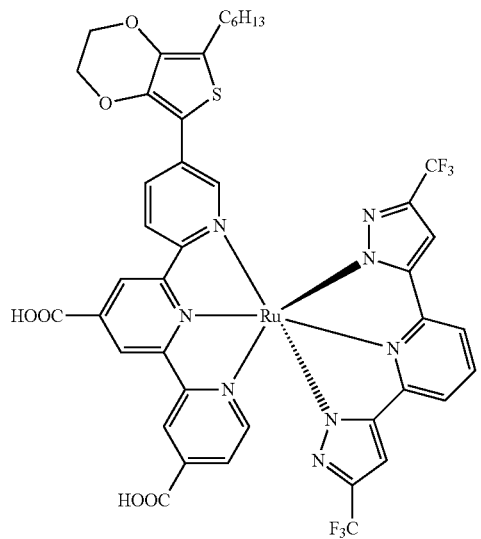
Example 15 (A-15)
TABLE 2
| Ruthenium complex | $E°_{ox}$ (V) | $E_{0-0}$ (V) | $E_{LUMO}$ (V) | Open circuit voltage ($V_{OC}$, V) | Short circuit current ($J_{SC}$, mA·cm$^{-2}$) | Filling factor (FF) | Photovoltaic conversion efficiency ($\eta$, %) |
|---|---|---|---|---|---|---|---|
| Ex. 1 | 0.85 | 1.66 | −0.81 | 750 | 16.97 | 0.715 | 9.10 |
| Ex. 2 | 0.85 | 1.66 | −0.81 | 760 | 19.69 | 0.686 | 10.27 |
| Ex. 3 | 0.83 | 1.79 | −0.96 | 759 | 19.76 | 0.658 | 9.88 |
| Ex. 4 | 0.83 | 1.78 | −0.95 | 640 | 13.36 | 0.711 | 6.08 |
| Ex. 5 | 0.81 | 1.79 | −0.98 | 650 | 14.10 | 0.723 | 6.63 |
| Ex. 8 | 0.97 | 1.67 | −0.70 | 640 | 12.24 | 0.728 | 5.70 |
| Ex. 9 | 0.96 | 1.69 | −0.73 | 630 | 12.78 | 0.722 | 5.81 |
| Ex. 10 | 0.91 | 1.65 | −0.74 | 710 | 18.81 | 0.690 | 9.22 |
| Ex. 11 | 0.88 | 1.78 | −0.90 | 720 | 15.72 | 0.726 | 8.39 |
| Ex. 12 | 0.83 | 1.66 | −0.83 | 650 | 12.97 | 0.723 | 6.09 |
| Ex. 13 | 0.85 | 1.66 | −0.81 | 720 | 17.83 | 0.690 | 8.86 |
| Ex. 14 | 0.93 | 1.78 | −0.85 | 700 | 17.02 | 0.690 | 8.35 |
| Ex. 15 | 0.90 | 1.78 | −0.88 | 710 | 16.22 | 0.700 | 8.22 |
| N749 | 0.88 | 1.66 | −0.78 | 750 | 17.18 | 0.692 | 8.92 |

As shown in FIGS. 1 and 2, the tridentate ligand of the present invention is superior to the conventional tridentate ligand contained in N749 (a conventional dye, also referred to as a black dye) in terms of extinction coefficient at a wavelength ranging from 200 nm to 400 nm. Specifically, the extinction coefficient of the tridentate ligands of synthesized Examples 4, 5, and 6 is as high as 45,000 $M^{-1}cm^{-1}$ or more at a wavelength ranging from 200 nm to 300 nm, and the extinction coefficient of the tridentate ligands of synthesized Examples 1, 9, and 10 is as high as 30,000 $M^{-1}cm^{-1}$ or more at a wavelength ranging from 300 nm to 400 nm. Therefore, the ruthenium complex produced from the tridentate ligand of the present invention can have superior absorption at a wavelength range of visible light, and the dye-sensitized solar cell produced thereby can absorb the visible light efficiently and can have a superior photovoltaic conversion efficiency.

As shown in FIGS. 3 and 4, the ruthenium complex of the present invention is comparable or superior to the conventional ruthenium complex contained in N749 in terms of extinction coefficient at a near infrared wavelength range. Specifically, the ruthenium complex of Examples 8 and 9 can still absorb light at a wavelength of about 750 nm, and the extinction coefficient thereof is superior to that of the conventional N749. The ruthenium complex of Example 13 is superior to the conventional N749 in terms of the extinction coefficient at a wavelength of 600 nm. The complex of Examples 1-5, 8, 9, 12, and 13 can absorb light at a near infrared light wavelength, and the extinction coefficient thereof at a visible light range is superior to that of the conventional sensitizer N749.

As shown in Table 2, the ruthenium complex of Examples 1-3 and 10 has electrical properties comparable to those of the conventional N749. Specifically, the photovoltaic conversion efficiency of the ruthenium complex of Examples 1-3 and 10 is superior to that of the conventional N749.

Additionally, the ruthenium complex of Examples 4, 5, 8, 9, 11, and 12 has electrical properties comparable to those of the conventional N749. Although the photovoltaic conversion efficiency of the ruthenium complex of these examples is inferior to that of the conventional N749, no thiocyanate ligand is contained in the ruthenium complex of these examples. Therefore, the ruthenium complex of these examples has a relatively strong coordination bonding strength, and thus can firmly chelate with ruthenium. Accordingly, the efficiency and the lifespan of the dye-sensitized solar cell produced thereby can be improved.

Similarly, the ruthenium complex of Examples 13-15 has the electrical properties and the photovoltaic conversion efficiency comparable to those of the conventional N749. However, since no thiocyanate ligand is contained in the ruthenium complex of these examples, the efficiency and the lifespan of the dye-sensitized solar cell produced by the ruthenium complex of these examples can be improved.

In view of the aforesaid, since the tridentate ligand of the present invention has enhanced conjugation, the light in the visible and near infrared wavelength range can be effectively absorbed by the tridentate ligand of the present invention. Therefore, the metal complex made from the tridentate ligand of the present invention has enhanced absorption in the visible and near infrared wavelength range, and the dye-sensitized solar cell produced thereby has improved photovoltaic conversion efficiency.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A 4,4'-dicarboxy-2,2'-bipyridine derived tridentate ligand represented by formula (I):

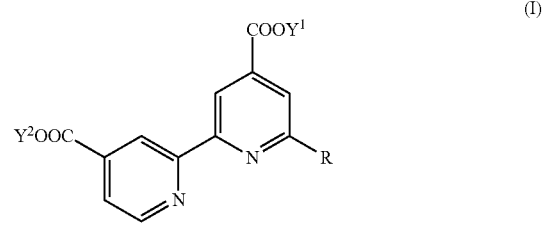

wherein $Y^1$ and $Y^2$ are independently selected from a group consisting of hydrogen and a $C_1$-$C_8$ straight or branched chain alkyl group; and R is selected from a group consisting of

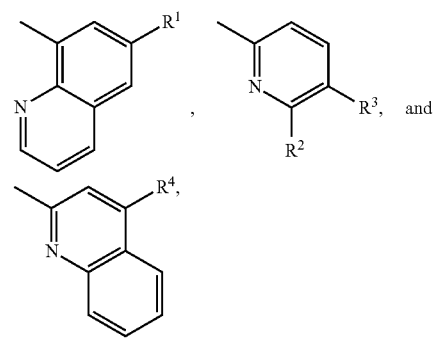

wherein $R^1$ and $R^4$ are independently selected from a group consisting of hydrogen, a halogen atom, trifluoromethyl, a carboxylic group, and a $C_1$-$C_{12}$ straight or branched chain alkyl group; and one of $R^2$ and $R^3$ is hydrogen, and the other of $R^2$ and $R^3$ is selected from a group consisting of a $C_1$-$C_{12}$ straight or branched chain alkyl group, an alkoxyl,

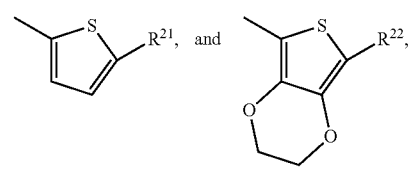

wherein $R^{21}$ and $R^{22}$ are independently selected from a group consisting of a $C_1$-$C_{12}$ straight or branched chain alkyl group, an alkoxy group, an alkylsulfenyl group, and

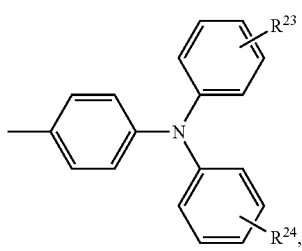

wherein
R²³ and R²⁴ are independently selected from a group consisting of hydrogen, a $C_1$-$C_{12}$ straight or branched chain alkyl group, an alkoxy group, and an alkylsulfenyl group.

2. The tridentate ligand as claimed in claim 1, wherein R represents

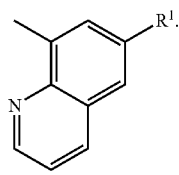

3. The tridentate ligand as claimed in claim 1, wherein R represents

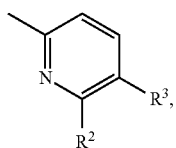

wherein $R^2$ is selected from a group consisting of

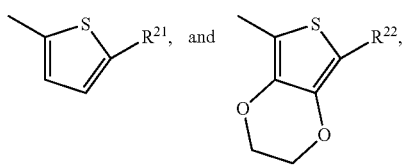

and $R^3$ is hydrogen.

4. The tridentate ligand as claimed in claim 3, wherein $R^2$ is

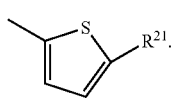

5. The tridentate ligand as claimed in claim 3, wherein $R^2$ is

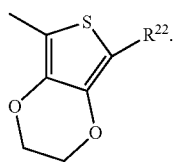

6. The tridentate ligand as claimed in claim 1, wherein R is

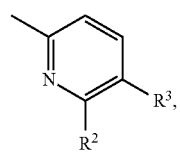

wherein $R^2$ is hydrogen, and $R^3$ is selected from a group consisting of $C_1$-$C_{12}$ straight or branched chain alkyl, alkoxyl group,

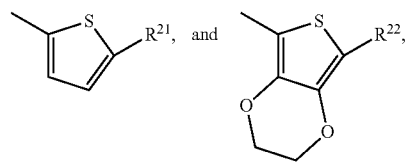

7. The tridentate ligand as claimed in claim 6, wherein $R^3$ is

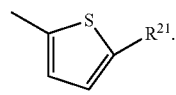

8. The tridentate ligand as claimed in claim 6, wherein $R^3$ is

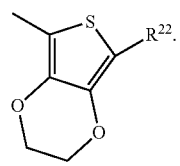

9. The tridentate ligand as claimed in claim 1, wherein R is

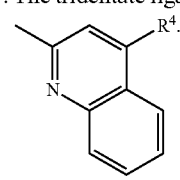

10. A metal complex represented by formula (II) or formula (III):

$$ML^1(L^2)_3 \qquad \text{(II), or}$$

$$ML^1L^3 \qquad \text{(III)}$$

wherein
M is selected from a group consisting of ruthenium and osmium;
$L^1$ represents a 4,4'-dicarboxy-2,2'-bipyridine derived tridentate ligand as claimed in claim 1;
$L^2$ represents a monodentate ligand; and
$L^3$ represents

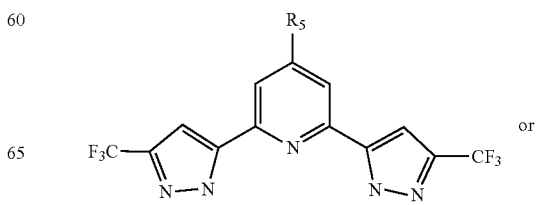

-continued

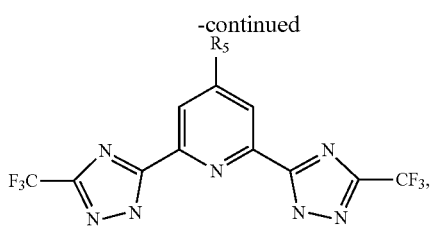

wherein
R⁵ is selected from a group consisting of hydrogen, a $C_1$-$C_8$ straight or branched chain alkyl group, an aryl group, an alkoxy group, an alkylsulfenyl group, a dialkylamino group, a functionalized alkanoyl group,

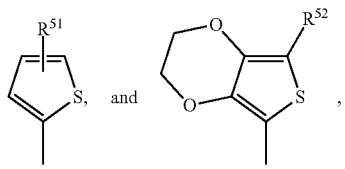

wherein
$R^{51}$ and $R^{52}$ are independently selected from a group consisting of a $C_1$-$C_{12}$ straight or branched chain alkyl group, an alkoxy group, and an alkylsulfenyl group.

11. The metal complex as claimed in claim 10, wherein $L^2$ is a thiocyanate group.

12. The metal complex as claimed in claim 10, wherein $R^{51}$ and $R^{52}$ are independently selected from a group consisting of a $C_1$-$C_{12}$ straight chain alkyl group, an alkoxy group, and an alkylsulfenyl group.

13. A dye-sensitized solar cell, comprising:

an electrolyte;

a first electrode disposed in said electrolyte, and including:

a transparent conductive substrate, a porous film disposed on said transparent conductive substrate, and a metal complex as claimed in claim 10 adsorbed on said porous film; and a second electrode disposed in said electrolyte and spaced apart from said first electrode.

* * * * *